US012286611B2

(12) United States Patent
Holenstein et al.

(10) Patent No.: US 12,286,611 B2
(45) Date of Patent: Apr. 29, 2025

(54) TISSUE CULTURE VESSEL FOR PREPARATION OF COMPRESSED HYDROGEL SKIN GRAFTS AND RELATED METHODS AND SYSTEMS

(71) Applicant: Cutiss AG, Schlieren (CH)

(72) Inventors: Claude Nicolas Holenstein, Zurich (CH); Vincent Ronfard, Villarzel (CH); Anna-Lena Dittrich, Zumikon (CH); Siegfried Graf, Kriens (CH); Christian Beyer, Olten (CH); Krzysztof Krasnopolski, Alpnach Dorf (CH); Diane Ledroit, Morges (CH); Gilles Weder, Cortaillod (CH); Roman Arnet, Ennetburgen (CH); Noa Schmid, Kriens (CH); Charles Coen, Villars-sur-Glane (CH)

(73) Assignee: Cutiss AG, Schlieren (CH)

( * ) Notice: Subject to any disclaimer, the term of this patent is extended or adjusted under 35 U.S.C. 154(b) by 0 days.

(21) Appl. No.: 18/571,777

(22) PCT Filed: Jun. 20, 2022

(86) PCT No.: PCT/IL2022/050656
§ 371 (c)(1),
(2) Date: Dec. 19, 2023

(87) PCT Pub. No.: WO2022/269601
PCT Pub. Date: Dec. 29, 2022

(65) Prior Publication Data
US 2024/0263116 A1     Aug. 8, 2024

Related U.S. Application Data

(60) Provisional application No. 63/240,360, filed on Sep. 2, 2021, provisional application No. 63/212,662, filed on Jun. 20, 2021.

(51) Int. Cl.
    *C12M 3/00*     (2006.01)
    *C12M 1/00*     (2006.01)
    (Continued)

(52) U.S. Cl.
    CPC ............ *C12M 21/08* (2013.01); *C12M 23/24* (2013.01); *C12M 23/26* (2013.01); *C12M 23/38* (2013.01);
    (Continued)

(58) Field of Classification Search
    None
    See application file for complete search history.

(56) References Cited

U.S. PATENT DOCUMENTS 5,843,766 A * 12/1998 Applegate .............. C12M 25/02
                                                      435/297.5
2002/0182720 A1* 12/2002 Gevaert ................. C12M 25/04
                                                      435/305.3

(Continued)

FOREIGN PATENT DOCUMENTS

KR     20110105057 A   *   9/2011
WO     WO 2021/176443 A1     9/2021

OTHER PUBLICATIONS

Braziulis et al., Modified Plastic Compression of Collagen Hydrogels Provides an Ideal Matrix for Clinically Applicable Skin Substitutes, 2012, Tissue Engineering: Part C, vol. 18 No. 6 (Year: 2012).*

(Continued)

*Primary Examiner* — Holly Kipouros
(74) *Attorney, Agent, or Firm* — Fenwick & West LLP; Daniel R. Brownstone

(57) ABSTRACT

A tissue culture vessel including a graft support tray (200) and a box having a lid (400) and a base which engages and retains the tray. The tray has two operational states: a first operational state in which a floor of the tray is slightly raised with respect to a floor of the base and a second operational state in which the floor of said tray descends to contact the floor of the base.

13 Claims, 35 Drawing Sheets

(51) Int. Cl.
*C12M 1/04* (2006.01)
*C12N 5/071* (2010.01)
*C12N 5/077* (2010.01)

(52) U.S. Cl.
CPC ............ *C12M 23/46* (2013.01); *C12M 23/50* (2013.01); *C12M 29/18* (2013.01); *C12N 5/0629* (2013.01); *C12N 5/0656* (2013.01); *C12N 5/0698* (2013.01); *C12N 2527/00* (2013.01); *C12N 2539/00* (2013.01)

(56) References Cited

U.S. PATENT DOCUMENTS

| | | | |
|---|---|---|---|
| 2008/0131473 A1* | 6/2008 | Brown | A61L 27/24 435/1.1 |
| 2012/0028234 A1 | 2/2012 | Guertin et al. | |
| 2016/0136333 A1 | 5/2016 | Reichmann | |
| 2019/0094208 A1* | 3/2019 | Vuong | C12M 21/08 |
| 2019/0249130 A1 | 8/2019 | Griffin et al. | |
| 2022/0380715 A1* | 12/2022 | Burgard | C12M 41/34 |

OTHER PUBLICATIONS

Haglund et al., Development of a Bioreactor for Axially Loaded Intervertebral Disc Organ Culture, 2011, Tissue Engineering: Part C, vol. 17 No. 10 (Year: 2011).*

Document titled KR20110105057A Apparatus for Growing Tissue Cultures in Vitro, machine translation of KR 20110105057 A provided by Espacenet, original document published 2011 (Year: 2011).*

PCT International Search Report and Written Opinion, PCT Application No. PCT/IL2022/050656, Dec. 8, 2022, 19 pages.

Instruction Manual ibidi Gas Incubation System for $CO_2$ and $O_2$, version 1.4, Apr. 11, 2017 (https://ibidi.com/img/cms/products/instruments/1_1192X_N_Gas_Incubation/IN_1192X_ibidi_Gas_Mixer_OEM.pdf).

* cited by examiner

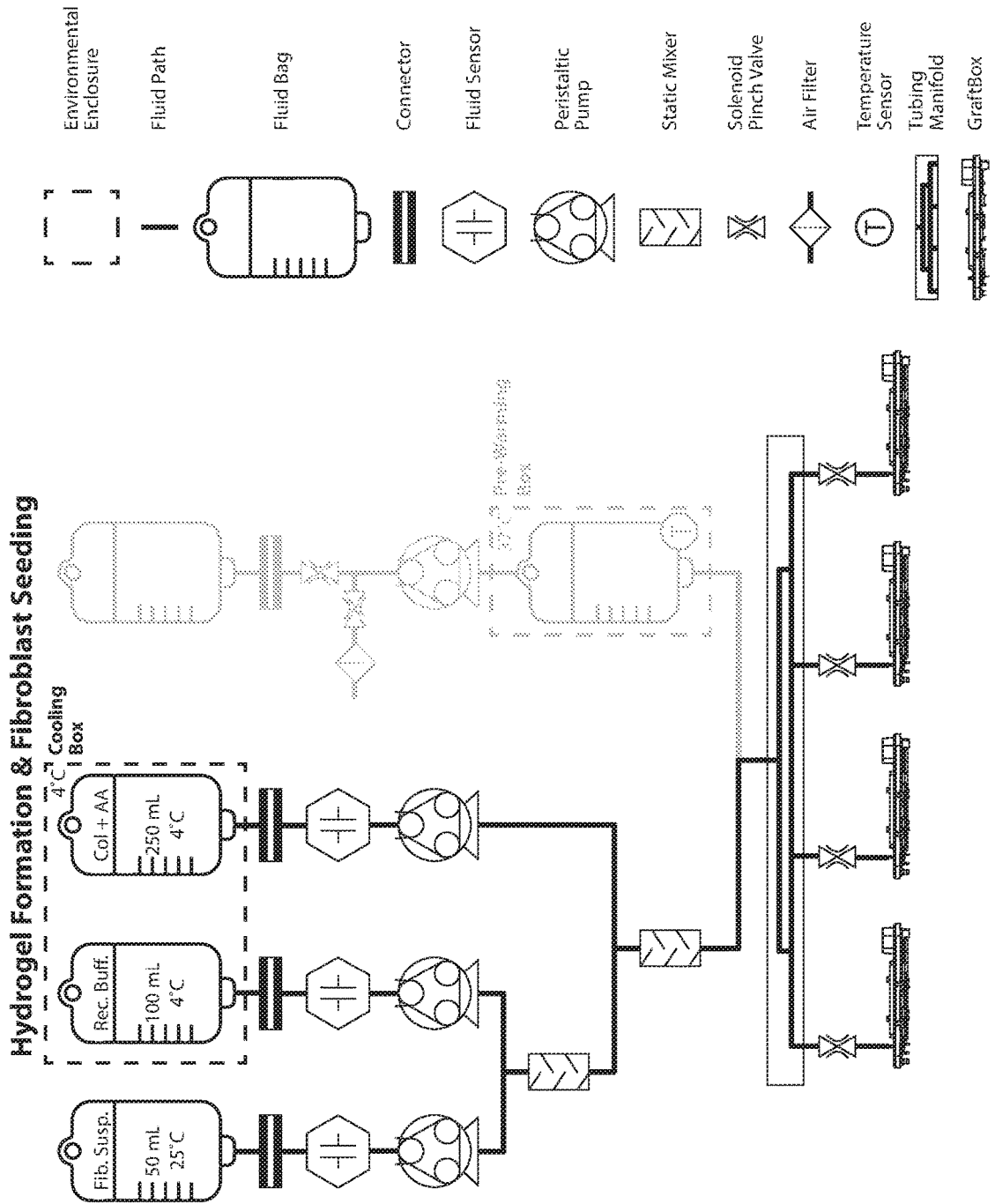
FIG. 8J2

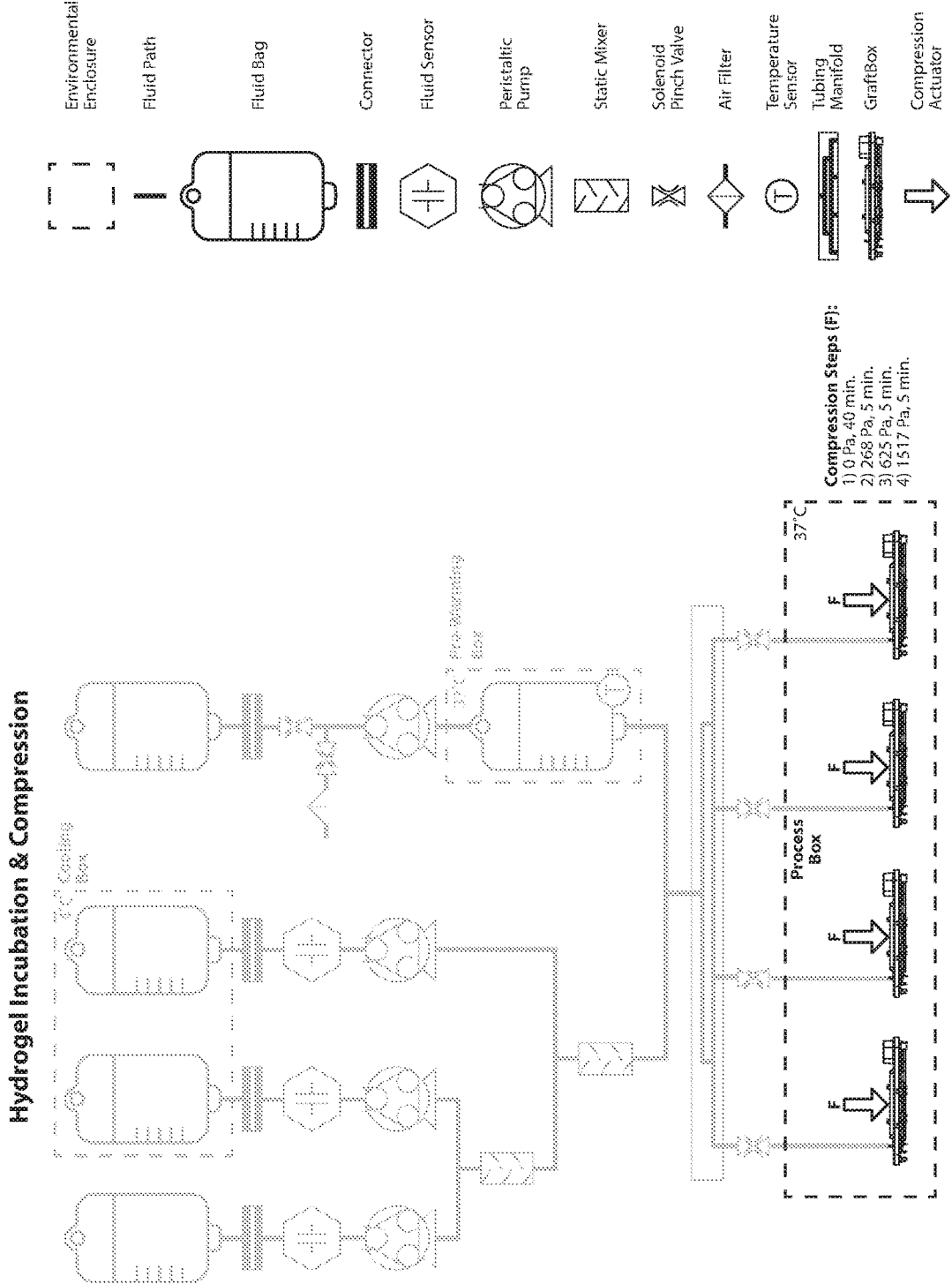
FIG. 8J3

TISSUE CULTURE VESSEL FOR PREPARATION OF COMPRESSED HYDROGEL SKIN GRAFTS AND RELATED METHODS AND SYSTEMS

RELATED APPLICATIONS

This PCT application claims the benefit according to 35 U.S.C. § 119(e) of U.S. provisional patent application 63/212,662 filed on Jun. 20, 2021 and of U.S. provisional patent application 63/240,360 filed on Sep. 2, 2021;

each of these earlier applications having the same title and applicant as the present application; and each of these earlier applications fully incorporated herein by reference.

FIELD OF THE INVENTION

The various described embodiments of the invention are in the field of tissue culture lab ware.

BACKGROUND OF THE INVENTION

Human skin is composed of three main layers: the epidermis (outermost), the dermis (middle) and the hypodermis (deeper most).

When a deep wound is created (full-thickness skin wound), after e.g. a burn accident, the epidermis and the full dermis (in some cases also the hypodermis) are damaged and surgical intervention is required.

Small full-thickness skin wounds are typically treated by means of full-thickness skin autografts in which epidermis and whole dermis are harvested from a healthy part of the body and transplanted onto the wound.

Large full-thickness skin wounds are typically treated by split-thickness skin autografts. The split-thickness skin autografts consist of epidermis and a thin and incomplete layer of dermis. Split-thickness skin autografts do not represent a satisfactory clinical solution to the problem of large full-thickness skin wounds. Large full-thickness skin wounds often heal badly and produce disfiguring and scars.

One reason that the full-thickness skin autografts heal deep wounds better than split-thickness autografts is that the full-thickness skin autografts include features that the split-thickness autografts do not, such as vascular structures. Vascular structures (blood and/or lymphatic vessels) provide oxygen and nutrients as well as immune cell trafficking and contribute to full functionality and tissue survival. Capillaries in the full-thickness skin grafts only need to connect to the capillaries of the wound bed, while in the case of split-thickness skin grafts, the capillaries need to grow from the wound bed into the graft in order to perfuse the tissue.

Additional reasons that the full-thickness skin autografts heal deep wounds better than split-thickness autografts are that transplanting split-thickness autografts onto full-thickness wounds can lead to tissue contraction which contributes to scarring and/or fibrosis and/or other disfiguring appearances. Alternatively or additionally, scarring can contribute to an inability of the grafted skin substitutes to grow with the patients (e.g. children), leading to further deterioration of the skin. As a result, use of split thickness autografts can require several consecutive surgeries over the span of several years to alleviate these issues. These additional surgeries impose large economic and psychological burdens on the patients.

More recently tissue engineering of skin has been used to create a substitute for full-thickness skin autografts. Tissue engineering employs a hydrogel as a scaffold material to provide a 3D cell substrate. The hydrogel is biocompatible and biomimetic, has low immunogenicity (conserved across species), and is naturally remodeled by cells which can be easily seeded interstitially within the fibril network. However, the poor mechanical properties of hydrogels are a limit to their clinical use as scaffolds for tissue engineering applications. Mechanical stability is important for the clinical application of engineered skin tissue based on hydrogels due to the relatively large area and thinness characteristic of skin grafts (a clinically relevant size for a skin graft is 50 $cm^2$ or more with a thickness of 2 mm or less).

Mechanical stability allows handling and processing of a hydrogel-based tissue engineered skin graft during and after culturing as well as during and after surgical application and/or testing. Mechanical stability of hydrogel can be increased by compaction.

SUMMARY OF THE INVENTION

A broad aspect of the invention relates to production and transport of a compressed hydrogel skin graft under sterile conditions in a single vessel.

One aspect of some embodiments of the invention relates to a sealed tissue culture vessel which includes a graft support frame in a box having a lid and a base. According to these embodiments the frame has two operational states: a first operational state in which the frame is slightly raised with respect to a floor of the base in which it resides, and a second operational state in which the frame descends to contact the floor of the base in which it resides. In some embodiments the lid includes a moveable plunger which, when depressed, moves the frame from the first to the second operational state. In some embodiments, the lid includes one or more surge compartments to accommodate media displaced from the frame when the plunger descends. In some embodiments, the surge compartments include gas permeable membranes on their upper surfaces. These gas permeable membranes permit air to escape from the vessel as the plunger descends and enter the vessel as the plunger rises. The gas permeable membranes permit an exchange of gases between the ambient environment and an interior of the vessel while maintaining sterility. In some embodiments the gas permeable membranes contribute to an ability to maintain sterility of contents of the vessel outside of a tissue culture hood. The gas permeable membranes also support gas exchange during cell culture, e.g. enriched (5% CO2) while being placed in an incubator with such a controlled gas environment.

Another aspect of some embodiments of the invention relates to a graft support tray with a media permeable membrane floor and external first normally extended springs which support the membrane floor in a raised position in the absence of an external force. In some embodiments a second set of normally extended springs in an opposite orientation is attached to the first springs. In some embodiments the first and/or second set of springs are leaf springs. In some embodiments the first and/or second springs are attached to two opposite sides of the frame. In some embodiments the frame includes guidance holes/pins that mate with corresponding pins/holes in the base and/or lid.

Yet another aspect of some embodiments of the invention relates to a base of the tissue culture vessel which is configured to accommodate the graft support frame. In some embodiments the base includes a compression structure which supports the membrane floor of the frame when it is fully descended but still permits flow of media outwards as the frame descends. In some embodiments, the base includes indentations to accommodate the first and/or second sets of springs of a frame seated in the base. In some embodiments, the base includes pins or holes that mate with comparable holes or pins provided on the frame. In some embodiments, these pins/holes help orient the frame within the base. Alternatively or additionally, in some embodiments, the base includes pins or holes that mate with comparable holes or pins provided on the plunger of the lid. In some embodiments, these pins/holes help orient the plunger with respect to the frame when the frame is seated in the base. In some embodiments, the lid or base includes an O-ring or other gasket. According to various exemplary embodiments of the invention this gasket is integrally formed as part of the lid or base. In some embodiments, the O-ring contributes to formation of an airtight seal. According to various exemplary embodiments of the invention, the base includes a waste drainage port and/or a sample removal port. In some embodiments, these ports are provided as barbed connectors. Alternatively or additionally, in some embodiments, the base includes snap to fit connectors for attachment to the lid. Alternatively or additionally, in some embodiments, the base includes mating snap inserts for a transport lock. In some embodiments, the transport lock holds the plunger in a partially descended position.

Still another aspect of some embodiments of the invention relates to a lid of the tissue culture vessel. In some embodiments the lid includes a rigid frame with a flexible bellows holding a plunger in a fixed orientation with respect to the frame. In some embodiments, the bellows is normally open so that it holds the plunger in a raised position in the absence of an external force. In some embodiments, the lid includes one or more raised surge compartments. In some embodiments, the surge compartments are fitted with gas permeable membranes on their upper surface. According to various exemplary embodiments of the invention, the membranes are placed on the inside or outside of the surge compartments.

In some embodiments, the rigid frame is provided with snap hooks that engage corresponding structures on the base. In some embodiments, the lid includes a series of external barbed connectors attached to internal outlet ports in relevant locations. For example, barbed connectors for $CO_2$/Air in and/or Fibroblasts (FB) and/or Media and/or Keratinocytes and/or Collagen hydrogel are provided. Alternatively or additionally, in some embodiments, an additional barbed port is provided for $CO_2$/Air out. Alternatively or additionally, in some embodiments, $CO_2$/Air leaves the tissue culture vessel via the gas permeable membranes of the surge compartment.

An additional aspect of some embodiments of the invention relates to tissue culture method in which hydrogel loaded with fibroblasts is introduced into a sealed tissue culture vessel and incubated to allow the fibroblasts to populate the gel matrix. After the hydrogel has been formed, it is then compressed while in the same sealed tissue culture vessel. Keratinocytes (KC) are then seeded in the same sealed tissue culture vessel and additional incubation is conducted until the graft is ready for transplantation. In some exemplary embodiments of the invention, hydrogel formation includes cross-linking by raising the PH (mixing the collagen/cell mix with a buffer). This process is sometimes referred to as polymerization although it is not a true polymerization.

A further additional aspect of some embodiments of the invention relates to a transport method for compressed hydrogel skin grafts in which the graft is grown in a sealed tissue culture vessel, growth media is removed and transport media is introduced, an integrated plunger of a lid of the sealed tissue culture vessel is partially lowered and locked in position.

Another further aspect of some embodiments of the invention, relates to a system for concurrent management and operation of tissue culture containers. In some embodiments, the tissue culture containers are graft culture containers. In some exemplary embodiments of the invention, the graft culture containers are as described hereinabove. In some exemplary embodiments of the invention, the system relies on a computerized controller to distribute cells and/or media and/or matrix material through conduits to the containers. In some embodiments the system controls mixing of mesenchymal cells (i.e. fibroblasts) with extra-cellular matrix molecules (e.g. collagen) and distributes the resultant cell/matrix mixture to culture vessels in a coordinated manner. In some embodiments, various compartments of the system are heated and/or cooled. In some embodiments, cooling of the cell matrix contributes to a reduction in premature gelation. Alternatively or additionally, in some embodiments $CO_2$ level and/or humidity are controlled in at least one system compartment.

Yet another further aspect of some embodiments of the invention, relates to a system that automatically changes media in a plurality of tissue culture containers. In some embodiments, the tissue culture containers are graft culture containers. In some exemplary embodiments of the invention, the graft culture containers are as described hereinabove. In some embodiments, the system employs a tilt mechanism.

Still another further aspect of some embodiments of the invention, relates to a system that automatically compresses extracellular matrix material (e.g. hydrogel) in a plurality of tissue culture containers. According to various exemplary embodiments of the invention the compression is conducted in parallel and/or in series.

Still another additional further aspect of some embodiments of the invention, relates to a system that provides visual images of cell cultures (e.g. graft cultures) at a remote location and allows remote manipulation of one or more culture parameters via a user interface at the remote location. In some embodiments, the visual images are captured by a camera and transmitted across a network to a smart device (e.g. phone or tablet). Alternatively or additionally, in some embodiments the user interface is a graphical user interface (GUI) of a smart device.

For purposes of this specification and the accompanying claims, the term "camera" includes conventional optical cameras as well as OCT (optical coherence tomograph) devices. In some exemplary embodiments of the invention, the camera does not magnify. In other exemplary embodiments of the invention, the camera magnifies an acquired image 2×, 5×, 10×, 50×, 100×, 250×, 500×, 1000× or intermediate or greater numbers of times. In some embodiments, magnification is achieved by attaching the camera to, or integration of the camera with, a microscope.

In some of the drawings an exemplary tissue culture vessels according to some embodiments of the invention is indicated as a "graftbox" (e.g. FIG. 8I or FIG. 8J) or "process box" (e.g. FIG. 12C).

It will be appreciated that the various aspects described above relate to solution of technical problems associated with folding and/or tearing of a skin graft during transportation from one location to another.

Alternatively or additionally, it will be appreciated that the various aspects described above relate to solution of technical problems related to reducing the need for a sophisticated tissue culture facility for production of a skin graft.

Alternatively or additionally, it will be appreciated that the various aspects described above relate to solution of technical problems related to producing a large amount of graft material (e.g. 1000 cm$^2$; 1500 cm$^2$; 2000 cm$^2$; 2500 cm$^2$; 3000 cm$^2$; 3500 cm$^2$; 4000 cm$^2$; 4500 cm$^2$; 5000 cm$^2$; 5500 cm$^2$ or intermediate or larger areas) from a small amount of biopsy material. According to various exemplary embodiments of the invention the graft area is 100 times, 150 times, 200 times, 250 times or intermediate or larger numbers of times larger than the area of the biopsy.

Alternatively or additionally, it will be appreciated that the various aspects described above relate to solution of technical problems related to remote management of tissue cultures.

Alternatively or additionally, it will be appreciated that the various aspects described above relate to solution of technical problems related to reducing a workload on a tissue culture technician.

Alternatively or additionally, it will be appreciated that the various aspects described above relate to solution of technical problems related to improving the robustness and reproducibility and/or reducing inter-batch variability of the graft manufacturing process.

Alternatively or additionally, it will be appreciated that the various technical aspects described above contribute to a reduction in the overall manufacturing cost.

Alternatively or additionally, it will be appreciated that the various aspects described above relate to solution of technical problems related to manufacturing the tissue graft in a closed automated box. This approach obviates a need for a heavy manufacturing suite and/or a cleanroom while preserving sterile conditions. As a result, homologous grafts can be manufactured in multiple sites such as a hospital where a patient is housed In some exemplary embodiments of the invention there is provided a tissue culture vessel including: (a) a graft support tray; (b) a box having a lid and a base, the box engaging and retaining the tray; wherein the tray has two operational states: a first operational state in which a floor of the tray is slightly raised with respect to a floor of the base; and a second operational state in which the floor of the tray descends to contact the floor of the base. In some embodiments the vessel includes a moveable plunger attached to the lid. Alternatively or additionally, in some embodiments the vessel includes one or more surge compartments. Alternatively or additionally, in some embodiments the vessel includes a gas permeable membrane on an upper surface of the surge compartment(s). Alternatively or additionally, in some embodiments the vessel is sterilized and wrapped to preserve sterility.

In some exemplary embodiments of the invention there is provided a graft support tray including: (a) a rigid frame; (b) a liquid permeable membrane floor attached to a lower edge of the frame; and (c) a first set of normally extended springs attached externally to two opposite sides of the frame. In some embodiments the tray includes a second set of normally extended springs in an opposite orientation attached to the first springs. Alternatively or additionally, in some embodiments the tray includes guidance holes/pins that mate with corresponding pins/holes in a base in which the frame is installed. Alternatively or additionally, in some embodiments the tray includes guidance holes/pins that mate with corresponding pins/holes a lid positioned over the support frame.

In some exemplary embodiments of the invention there is provided a base of a tissue culture vessel including: a compression structure designed and configured to support a membrane floor of a graft support frame fully descended in the base; the compression structure constructed to permit flow of media outwards as the frame descends. In some embodiments the vessel includes indentations sized and positioned to accommodate one set of springs of a graft support tray seated in the base. Alternatively or additionally, in some embodiments the vessel includes indentations sized and positioned to accommodate two set of springs of a graft support tray seated in the base. Alternatively or additionally, in some embodiments the vessel includes pins or holes sized and positioned to engage corresponding holes or pins provided on a graft support tray positioned in the base. Alternatively or additionally, in some embodiments the vessel includes pins or holes sized and positioned to engage corresponding holes or pins provided on a plunger of a lid fitted to the base. Alternatively or additionally, in some embodiments the vessel includes an O-ring or other gasket or an overmolded elastomer. Alternatively or additionally, in some embodiments the vessel includes at least one liquid removal port. Alternatively or additionally, in some embodiments at least one of the at least one port includes a barbed connector. Alternatively or additionally, in some embodiments the vessel includes snap to fit connectors for attachment to a lid. Alternatively or additionally, in some embodiments the vessel includes mating snap inserts for a transport lock.

In some exemplary embodiments of the invention there is provided a lid of a tissue culture vessel including: (a) a rigid frame; and (b) a flexible bellows deployed within the frame, the bellows holding a plunger in a fixed orientation with respect to the frame. In some embodiments the bellows is normally open so that it holds the plunger in a raised position in the absence of an external force. Alternatively or additionally, in some embodiments the lid includes one or more surge compartments extending above a plane of an upper edge of the frame. Alternatively or additionally, in some embodiments the lid includes gas permeable membranes on an upper surface of the surge compartment(s). Alternatively or additionally, in some embodiments the lid includes snap hooks on the rigid frame sized and positioned to engage a base covered by the lid. Alternatively or additionally, in some embodiments the lid includes one or more external barbed connectors in fluid communication with internal outlet ports. Alternatively or additionally, in some embodiments the lid includes a barbed port for $CO_2$/AIR out. Alternatively or additionally, in some embodiments the lid includes an elastomeric seal on a side of the lid which contacts a base when the vessel is assembled.

In some exemplary embodiments of the invention there is provided a skin graft production method including: (a) introducing hydrogel containing fibroblasts (FB) into a sealed tissue culture vessel; (b) incubating until the FB populate the gel matrix; (c) compressing the gel matrix in the same sealed tissue culture vessel; (d) seeding keratinocytes (KC) onto the compressed matrix in the same sealed tissue culture vessel; and (e) incubating further until the graft is formed and ready for transplantation. In some embodiments the method includes visually monitoring growth of the FB and/or the KC within the tissue culture vessel using a microscope. Alternatively or additionally, in some embodiments the method includes exchanging culture media, wherein the exchanging includes: tilting the sealed tissue culture vessels in one direction to cause media to flow into a surge compartment; and tilting the sealed tissue culture vessels in a second direction to remove the media via gravitational flow to a waste container.

In some exemplary embodiments of the invention there is provided a skin graft production method including: (a) preparing compressed hydrogel skin grafts in sealed tissue culture vessels at a first location: (b) removing growth media and introducing transport media to the sealed tissue culture vessels; (c) partially lowering integrated plungers in lids of the sealed tissue culture vessels and locking in position; and (d) transporting to a second location. In some embodiments the removing includes: tilting the sealed tissue culture vessels in one direction to cause media to flow into a surge compartment; and tilting the sealed tissue culture vessels in a second direction to remove the media via gravitational flow to a waste container.

In some exemplary embodiments of the invention there is provided a transport lock including: (a) a spanning member sized to conform to dimensions of the tissue culture vessel as described above and having: (i) on its lower edge two notches configured to conform to a profile of a frame of the lid; (ii) a downward extension between the notches; and a clasp sized to engage and retain a snap to fit connector on the base on an outward edge of each of the notches; and (iii) a series of slots on its upper edge, the slots sized and positioned to engage and retain corresponding ribs on a lower surface of a base of a second tissue culture vessel as described above positioned above.

In some exemplary embodiments of the invention there is provided an assembly including: a plurality of culture vessels as described above arranged in a vertical array with transport locks as described above interspersed between them.

In some exemplary embodiments of the invention there is provided a system including: (a) a plurality of graft culture containers; (b) reservoirs for cell suspension(s), gel matrix material and culture media; (c) conduits connecting each of the reservoirs to each of the culture containers; (d) a controller configured to deliver the cell suspension(s), gel matrix material and culture media through the conduits to the culture containers in a coordinated manner to produce grafts. In some embodiments, the reservoirs for cell suspensions include at least one fibroblast (FB) reservoir and at least one keratinocyte (KC) reservoir. Alternatively or additionally, in some embodiments the reservoirs for cell suspensions include at least two reservoirs for at least two different cell types selected from the group consisting of fibroblasts (FB), keratinocytes (KC), adipocytes, myocytes, neuronal cells, pericytes, stem cells, and Induced Pluripotent Cells (IPCs). Alternatively or additionally, in some embodiments the reservoirs for cell suspensions include at least two reservoirs for at least a first cell type of epithelial origin and a second cell type selected from the group consisting of cells of mesenchymal cells, cells of dermal origin, adipocytes, myocytes, neuronal cells, pericytes and stem cells. Alternatively or additionally, in some embodiments the system includes valves in the conduits under control of the controller. Alternatively or additionally, in some embodiments the reservoir for the gel matrix includes a cooling element. Alternatively or additionally, in some embodiments the controller includes pumps to move the cell suspension(s), gel matrix material and culture media through the conduits. Alternatively or additionally, in some embodiments the system includes a heater positioned to heat the culture media. Alternatively or additionally, in some embodiments the system includes a mixing module that receives cells from one reservoir and gel matrix from a different reservoir and mixes cells into the matrix to produce a gel matrix cell suspension. Alternatively or additionally, in some embodiments the mixing module mixes cells from one reservoir with buffer from a second reservoir to produce a buffered cell suspension and then mixes the buffered cell suspension with gel matrix from a third reservoir to produce a gel matrix cell suspension. Alternatively or additionally, in some embodiments the system includes an incubation chamber designed and configured to contain the plurality of graft culture containers. Alternatively or additionally, in some embodiments the system includes a compression mechanism operable by the controller to compress a gel matrix in one or more of the graft culture containers. Alternatively or additionally, in some embodiments the system includes a camera and bidirectional data communication link to an external input device. Alternatively or additionally, in some embodiments the controller is adapted to periodically remove media from the graft culture containers and add new media from one of the reservoirs. Alternatively or additionally, in some embodiments each of the graft culture containers includes a tissue culture vessel as described hereinabove.

In some exemplary embodiments of the invention there is provided a system including: (a) a plurality of cell culture containers; (b) reservoirs for cell suspension and culture media; (c) conduits connecting each of the reservoirs to each of the culture containers; and (d) a controller configured to deliver the cell suspension and culture media through the conduits to the culture containers in a coordinated manner to produce cultures in the containers. In some embodiments, the reservoirs for cell suspensions contain at least one cell type selected from the group consisting of fibroblasts (FB), keratinocytes (KC), adipocytes, myocytes, neuronal cells, pericytes and stem cells. Alternatively or additionally, in some embodiments the reservoirs for cell suspensions contain a first cell type of epithelial origin and a second cell type selected from the group consisting of cells of mesenchymal cells, cells of dermal origin, adipocytes, myocytes, neuronal cells, pericytes and stem cells. Alternatively or additionally, in some embodiments the reservoirs for the cell suspension and culture media include a temperature control mechanism. Alternatively or additionally, in some embodiments the controller includes pumps (932) to move the cell suspension (s) and culture media through the conduits. Alternatively or additionally, in some embodiments the system includes connectors for attachment of the conduits to the cell culture containers. Alternatively or additionally, in some embodiments the system includes an incubation chamber designed and configured to contain the plurality of cell culture containers. Alternatively or additionally, in some embodiments the system includes a camera and bidirectional data communication link (982) to an external input device. Alternatively or additionally, in some embodiments the controller is adapted to periodically remove media from the cell culture containers and add new media from one of the reservoirs.

In some exemplary embodiments of the invention there is provided a system including: (a) a cell culture container equipped with at least one port; (b) a detector measuring a parameter of media in the container and producing an indicator signal; and (c) a media exchange mechanism including a controller configured to respond to a threshold value of the indicator signal by operating a pump that withdraws spent media via the at least one port and introduces fresh media via the at least one port. In some embodiments, the parameter is selected from the group consisting of pH, $CO_2$ concentration, glucose concentration, lactate concentration and non adherent cells (number and/or percentage). Alternatively or additionally, in some embodiments the detector includes a pH electrode and/or a camera. Alternatively or additionally, in some embodiments the cell culture container includes a graft culture vessel as described hereinabove.

In some exemplary embodiments of the invention there is provided a system including: (a) a closed cell culture container equipped with at least one gas port; (b) a $CO_2$ tank connected via a regulator to the at least one gas port; and (c) a water reservoir though which $CO_2$ from the tank passes between the regulator and the at least one gas port. In some embodiments, the closed cell culture container includes a graft culture vessel as described hereinabove.

In some exemplary embodiments of the invention there is provided a system including: (a) a support surface for a plurality of graft culture vessels; (b) a tilt mechanism controlling an angle of the support surface; and (c) a controller configured to operate the mechanism to provide controlled removal of media from the vessels through one or more ports. In some embodiments, the support surface is installed in an incubation chamber as described hereinabove. Alternatively or additionally, in some embodiments the controller is configured to operate the tilt mechanism to +18°, and then to −30° to drain media into a waste container. Alternatively or additionally, in some embodiments the controller is configured to operate the tilt mechanism to −5° to facilitate sampling. Alternatively or additionally, in some embodiments the controller is configured to operate the tilt mechanism to +18° to remove media from the top compartment into a surge compartment, and then to −30° to drain all media.

In some exemplary embodiments of the invention there is provided a system including: (a) a plurality of graft culture containers, each container having a movable plunger in a lid thereof; (b) at least one piston; and (c) a controller configured to operate a vertical displacement mechanism to lower and raise the at least one piston to depress and release each of the plungers in the lids of the containers. In some embodiments the system includes a horizontal displacement mechanism, wherein the controller aligns the at least one piston with the plungers. Alternatively or additionally, in some embodiments the vertical displacement mechanism is adjustable for different forces and compression patterns (e.g. linear, stepwise). Alternatively or additionally, in some embodiments the controller is programmable. Alternatively or additionally, in some embodiments the system includes a pressure sensor. Alternatively or additionally, in some embodiments the system includes a camera on the piston.

In some exemplary embodiments of the invention there is provided a system including: (a) a tissue culture container including at least one port; (b) a camera providing image output of a culture in the container; and (c) a controller exercising control over a media exchange mechanism. In some embodiments, the system includes a remote device receiving the image output and equipped with a user interface for operation of the controller. Alternatively or additionally, in some embodiments the media exchange mechanism includes at least one pump that withdraws spent media via at least one port and introduces fresh media via the at least one port. Alternatively or additionally, in some embodiments the media exchange mechanism includes a tilt mechanism controlling an angle of a support surface holding the tissue culture container.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIG. 8J2 is a simplified pictorial flow diagram of hydrogel formation and Fibroblast seeding according to an exemplary embodiment of the invention;

FIG. 8J3 is a simplified pictorial flow diagram of hydrogel incubation and compression according to an exemplary embodiment of the invention;

DETAILED DESCRIPTION OF EMBODIMENTS

Embodiments of the invention relate to tissue culture vessels configured for production of skin grafts and related methods.

Specifically, some embodiments of the invention can be used to produce a skin graft in a closed vessel. In some embodiments the vessel is completely aseptically closed and is intended for single use (disposable) to restrict contamination and to support operation in a low-grade GMP cleanroom class such as C or D according to EU GMP regulations.

The principles and operation of a tissue culture vessel and/or method according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Tissue Culture Vessel Overview

Figure 1A:
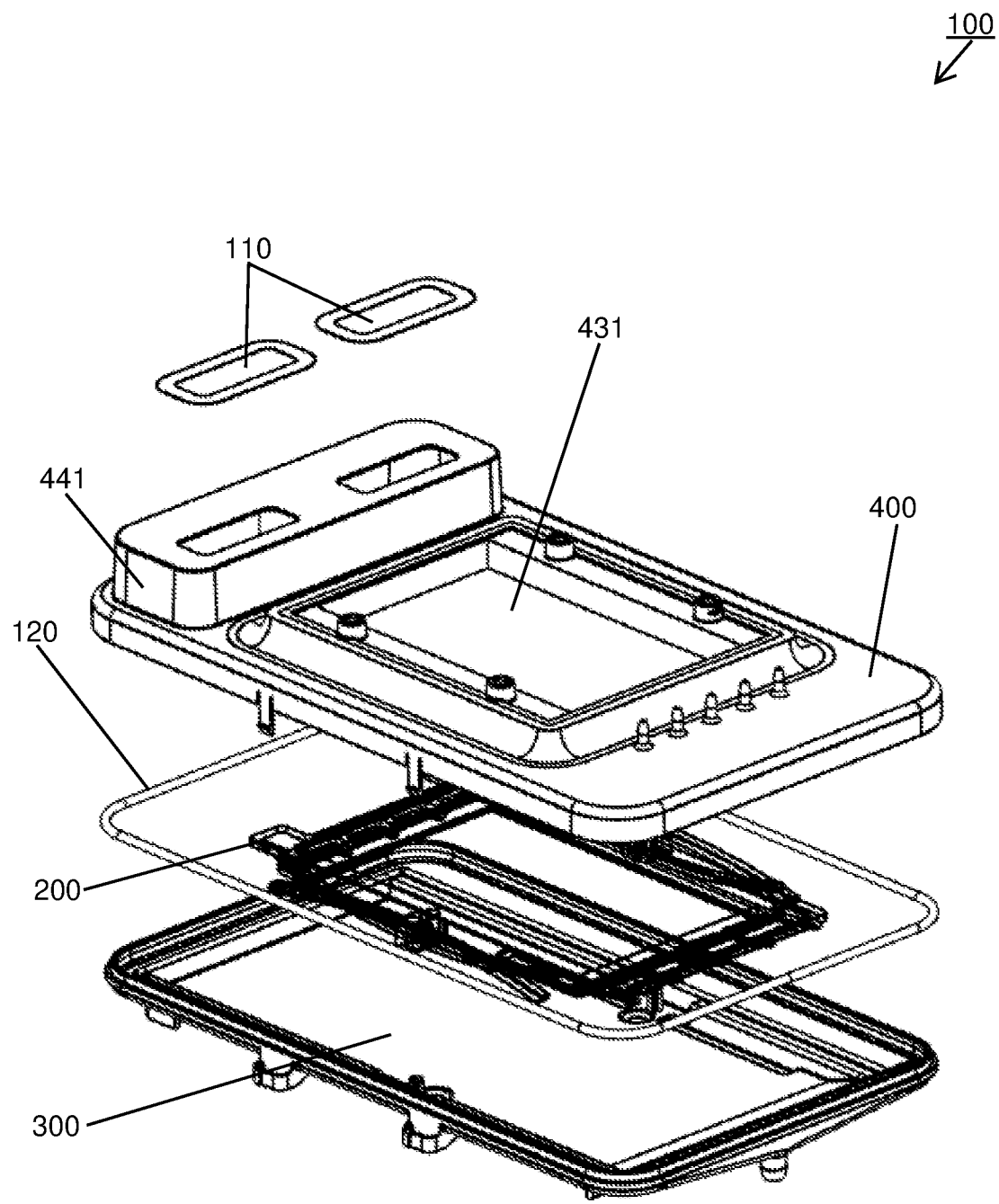
FIG. 1A is an exploded view of a tissue culture vessel according to some exemplary embodiments of the invention.

FIG. 1A is an exploded view of a tissue culture vessel, indicated generally as 100 according to some exemplary embodiments of the invention.

Depicted exemplary tissue culture vessel 100 includes a graft support tray 200, a box having a lid 400 and a base 300. In the depicted embodiment, the box engages and retains frame 210 (see FIG. 2A) of tray 200 which has two operational states. In a first operational state, tray 200 is slightly raised with respect to a floor of base 300. In a second operational state, tray 200 descends to contact the floor of base 300. In some embodiments, tray 200 is normally in the first operational state and moves to the second operational state in response to an external force. In the depicted embodiment, vessel 100 includes a moveable plunger 431 attached to lid 400. In some embodiments, depression of plunger 431 by an external force switches tray 200 to the second operational state. For purposes of this specification and the accompanying claims, the term "slightly raised" means there is sufficient space between tray 200 and floor of base 300 for liquid media to enter the space.

Depicted exemplary vessel 100 includes one or more surge compartments 441. In some embodiments, surge compartments 441 accommodate media displaced from tray 200 when plunger 431 descends and/or when the whole vessel 100 is tilted so that surge compartments 441 are below the rest of the vessel.

Depicted exemplary vessel 100 includes a gas permeable membrane 110 on an upper surface of surge compartment(s) 441. According to various exemplary embodiments of the invention, gas permeable membrane 110 is attached on the inside or outside of the surge compartment. Gas permeable membrane(s) 110 permit air to escape from vessel 100 as plunger 431 descends and enter the vessel as plunger 431 rises and/or permit an exchange of gases between the ambient environment and an interior of vessel 100 while maintaining sterility.

In some exemplary embodiments of the invention, vessel 100 is sterilized and wrapped to preserve sterility. For example, one or more vessels 100 are assembled and wrapped in a plastic sleeve then X-ray sterilized. In some embodiments connections to vessel 100 are made through sterile tube connections (e.g. tube welding) so that under normal use conditions exposure of the interior of the vessel to the environment does not occur until the graft is removed for transplantation or other use.

In the depicted embodiment, an O-ring 120 is used to provide an airtight seal between lid 400 and base 300. In other exemplary embodiments of the invention, O-ring 120 is replaced by a gasket or directly over-molded onto base 300 and/or lid 400.

Figure 1B:
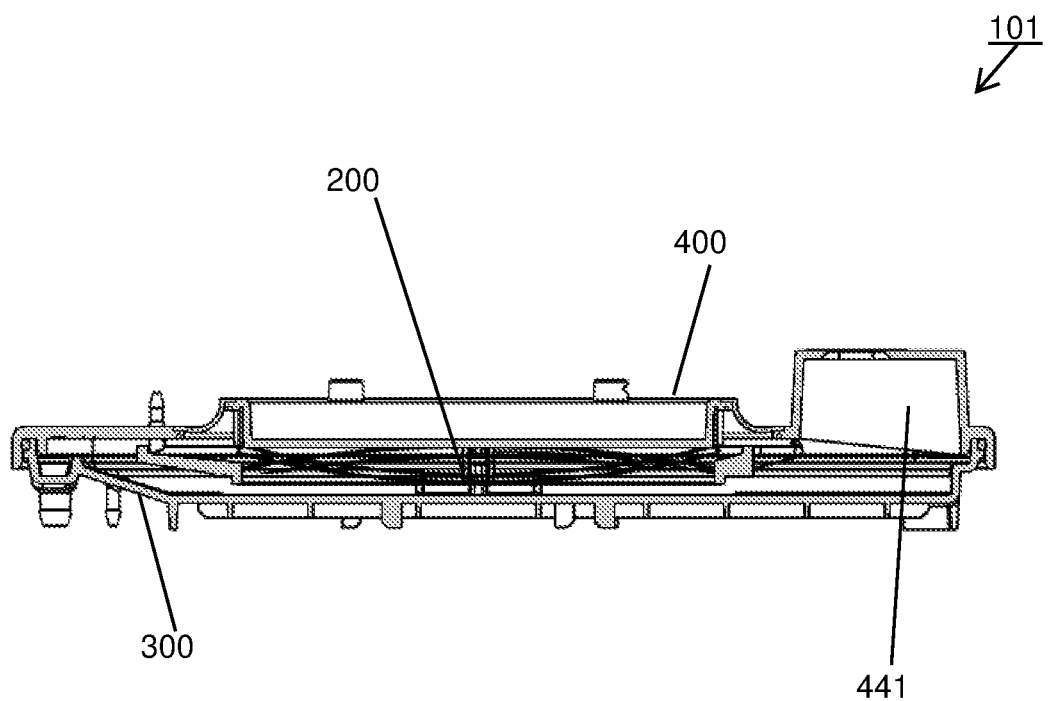
FIG. 1b is lateral cross section of an assembled tissue culture vessel as in FIG. 1A.

Each of graft support tray 200, base 300 and lid 400 are described in greater detail hereinbelow. Features used to characterize these individual parts also characterize vessel 100. FIG. 1b is lateral cross section, indicated generally as 101, of an assembled tissue culture vessel as in FIG. 1A illustrating interaction between the parts.

Exemplary Support Tray

Figure 2A:
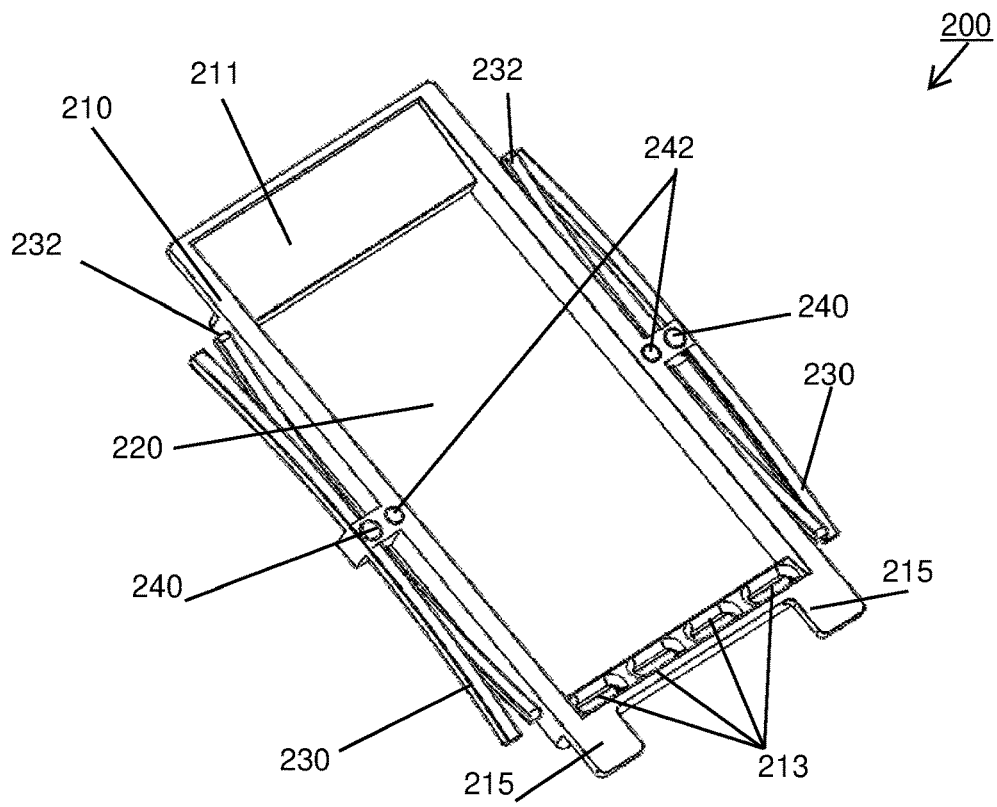
FIG. 2A is a top perspective view of a graft support tray according to some exemplary embodiments of the invention.

FIG. 2A is a top perspective view of a graft support tray, indicated generally as 200, according to some exemplary embodiments of the invention.

Figure 2B:
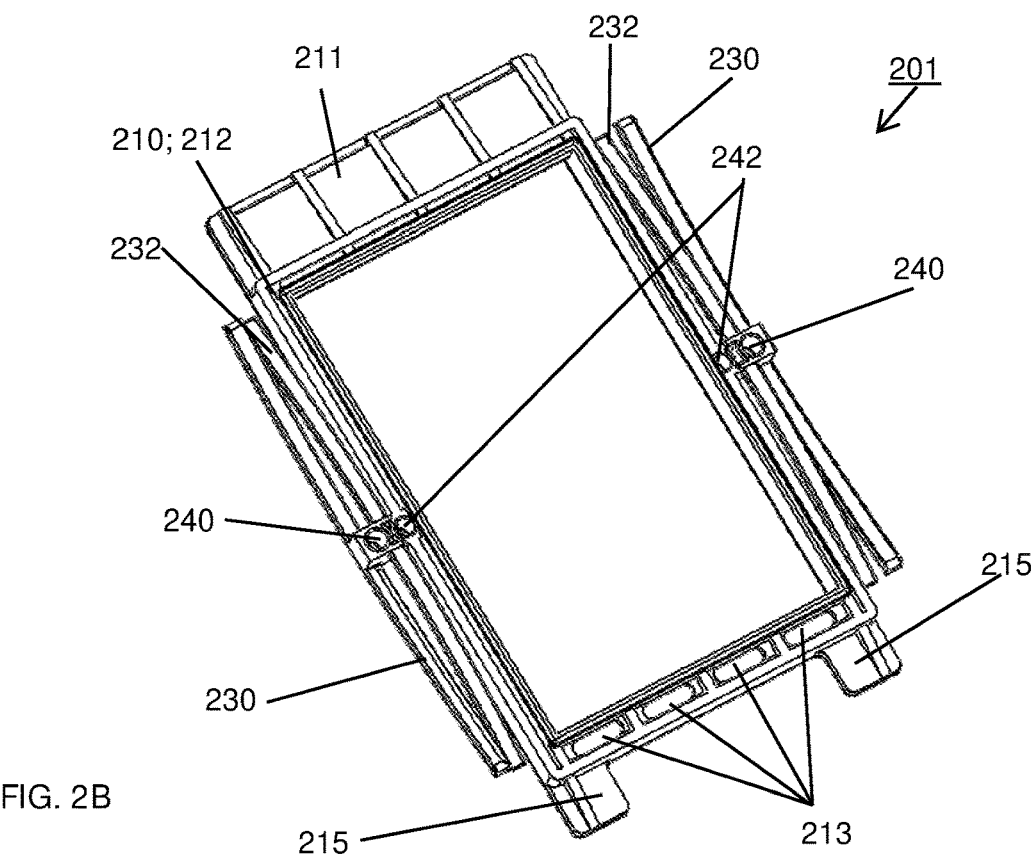
FIG. 2B is a bottom perspective view of the graft support tray of FIG. 2A.

FIG. 2B is a bottom perspective view, indicated generally as 201, of the graft support tray of FIG. 2A.

In the depicted embodiment, graft support tray 200 includes a rigid frame 210, a liquid permeable membrane floor 220 attached to a lower edge 212 (FIG. 2B) of frame 210 and a first set of normally extended springs 230 attached externally to two opposite sides of frame 210. Springs 230 function to support membrane floor 220 in a raised position in the absence of an external force as described in "first operational state" in the context of FIG. 1 hereinabove.

In the depicted embodiment, graft support tray 200 includes a second set of normally extended springs 232 in an opposite orientation attached to first springs 230. In some embodiments the first and/or second springs are attached to two opposite sides of the frame. In the depicted embodiment, springs 230 and 232 are leaf springs. In other exemplary embodiments of the invention, one or both of these sets of springs are provided as coil springs.

In the depicted embodiment, graft support tray 200 includes guidance holes/pins (240) that mate with corresponding pins/holes in a base in which the frame is installed.

In the depicted embodiment, graft support tray 200 includes guidance holes/pins (242) that mate with corresponding pins/holes a lid positioned over the support frame.

In some embodiments a ramp 211 is located on one side of graft support tray 200. In embodiments which feature a ramp 211, the ramp guides the injected liquids flowing into the region with the membrane floor 220. In some embodiments an angle of the ramp is 2°; 3°; 4°; 5°; 6°; 7° or 8° or intermediate or greater numbers of degrees. Alternatively or additionally, in some embodiments a length of ramp 211 is determined by an arrangement of the liquid inputs 460 and the size of the membrane 420.

Alternatively or additionally, in some embodiments on the other side of the graft support tray 200, a structure with holes 213 is located which enables efficient draining during overflowing or tilting.

The graft support tray 200 is in the assembled state prestressed via four spacers 411 (two are visible in FIG. 4A) in the lid which press on two ears 215 leveled with the rigid frame 210.

The rigid frame 210 is designed to be flat and to provide improved support to the bonded membrane 220.

The rigid frame 210 shown in the figures is designed with two walls and ribs in between to increase the stiffness which is required to ensure membrane 220 flatness.

Exemplary Base

Figure 3A:
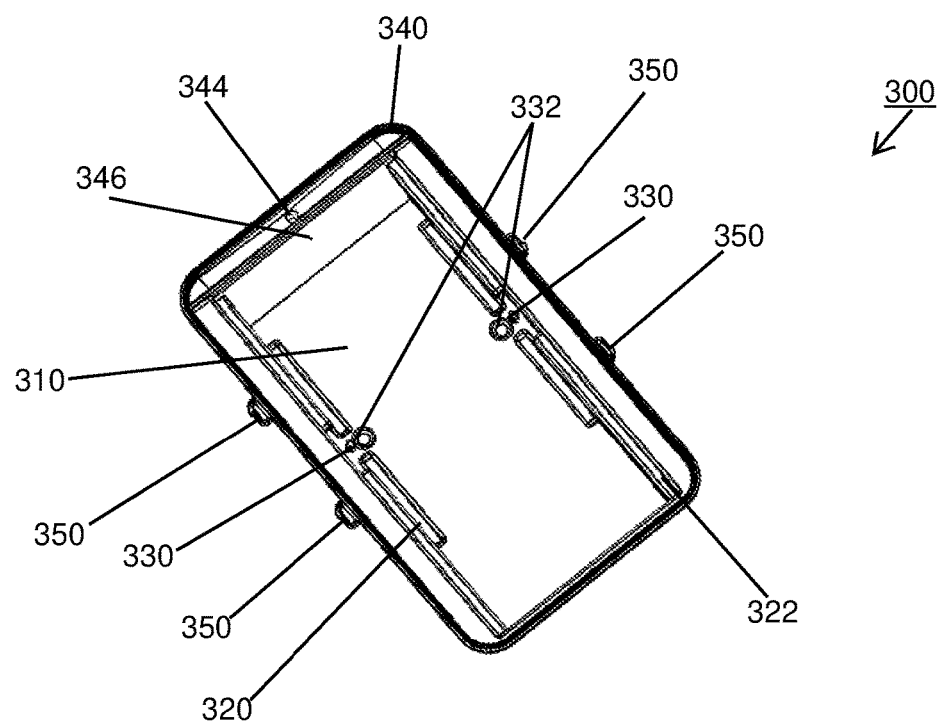
FIG. 3A is a top perspective view of a base of a tissue culture vessel according to some exemplary embodiments of the invention.

FIG. 3A is a top perspective view of a base, indicated generally as 300, of a tissue culture vessel base according to some exemplary embodiments of the invention.

Figure 3B:
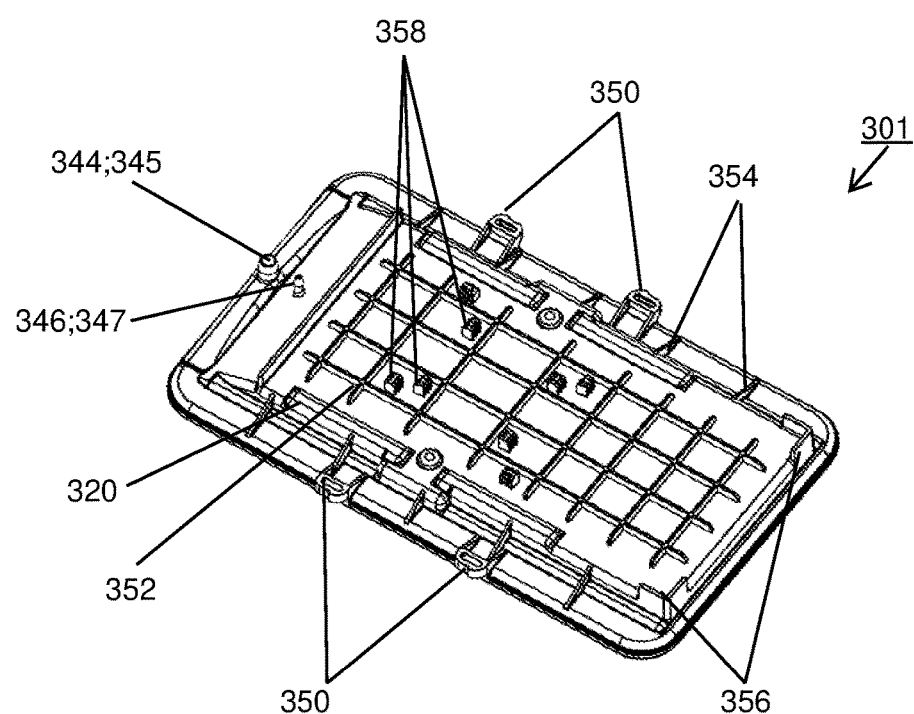
FIG. 3B is a bottom perspective view of the base of a tissue culture vessel of FIG. 3A.

FIG. 3B is a bottom perspective view, indicated generally as 301, of the base of a tissue culture vessel of FIG. 3A.

Figure 3C:
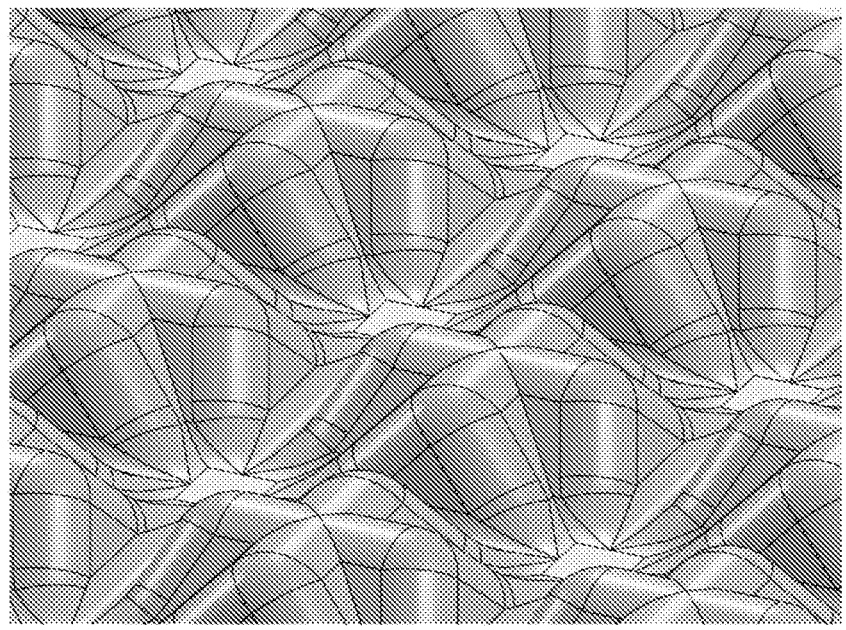
FIG. 3C is a schematic detail view of an exemplary compression structure according to some exemplary embodiments of the invention.
Figure 3D:
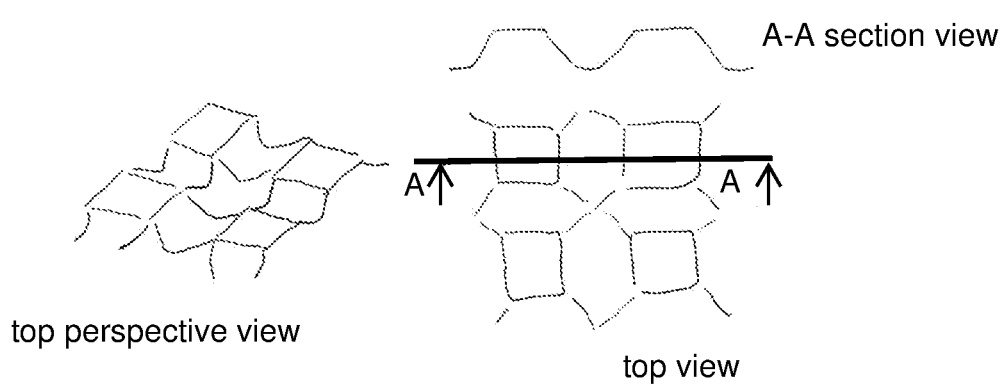
FIG. 3D is a schematic detail of an exemplary compression structure according to some exemplary embodiments of the invention from the top (lower right), section through line A-A (upper right), and top perspective (left side)

Depicted exemplary base 300 includes a compression structure 310 designed and configured to support a membrane floor of a graft support frame fully descended in the base. When base 300 is assembled in a tissue culture vessel 100, as the plunger 431 of the lid descends and forces the graft support tray downwards, media passes through compression structure 310 and into surge compartments (441 and/or 440; FIG. 1 and FIG. 4 respectively). In some exemplary embodiments of the invention, compression structure 310 is provided as a pattern molded into the base that allows media to flow to the surge compartments during compression. According to these embodiments, the pattern includes channels to facilitate liquid flow. FIG. 3C and FIG. 3D provide detail views of exemplary compression structurers 310. In other exemplary embodiments of the invention, compression structure 310 is constructed of liquid permeable material. In either case, compression structure 310 permits flow of media outwards as said frame descends.

According to various exemplary embodiments of the invention compression is achieved through the application of appropriate weights and/or application of an external linear force-controlled or displacement-controlled drive.

Depicted exemplary base 300 includes indentations 320 sized and positioned to accommodate one set of springs of a graft support tray seated in base 300. In the depicted embodiment, base 300 includes indentations (320) sized and positioned to accommodate two set of springs of a graft support tray seated in the base. In the depicted embodiment, base 300 includes an elevation 322 where the graft support tray is seated.

Depicted exemplary base 300 includes pins 330 or holes sized and positioned to engage corresponding holes or pins provided on a graft support tray positioned in the base. In some embodiments these pins/holes help orient the graft support tray within the base. In some embodiments, orientation of the graft support tray within base 300 contributes to accuracy of alignment of the graft support tray with a plunger 431 in the lid.

Depicted exemplary base 300 includes pins and/or holes 332 sized and positioned to engage corresponding holes or pins provided on a plunger of a lid fitted to base 300. In some embodiments these pins or holes 332 help orient the plunger with respect to the frame when the frame is seated in base 300. In some embodiments holes 332 are simple recessions to make space for the pins in the plunger. According to these embodiments, the pins 470 in the plunger engage with the graft support tray 200 guidance hole 242.

In the depicted embodiment, base 300 includes an O-ring 340 or other gasket or overmolded elastomeric structure. In some embodiments, O-ring 340 (or gasket) contributes to formation of an airtight and/or watertight seal.

In the depicted embodiment, base 300 includes at least one liquid removal port 344 and/or 346. In the depicted embodiment, port 344 is a waste drainage port and 346 is a sample removal port. FIG. 3B shows these ports are fitted with barbed connectors 345 and 347.

In the depicted embodiment, base 300 include snap to fit connectors 350 for attachment to a lid. In some embodiments lid 400 snaps into connector 350 while the transport lock clicks to the outside of the same connector structure.

In some exemplary embodiments of the invention, base 300 includes mating snap inserts 350 for a transport lock. In some embodiments the transport lock holds a plunger of a lid attached to a base in a partially descended position.

Also visible in FIG. 3B are ribs 352 and braces 354 for structural support and/or strength, legs 356 and stacking spacers 358.

Additional details on the transport lock are provided hereinbelow in the context of FIG. 7A, FIG. 7B and FIG. 7C.

Exemplary Lid

Figure 4A:
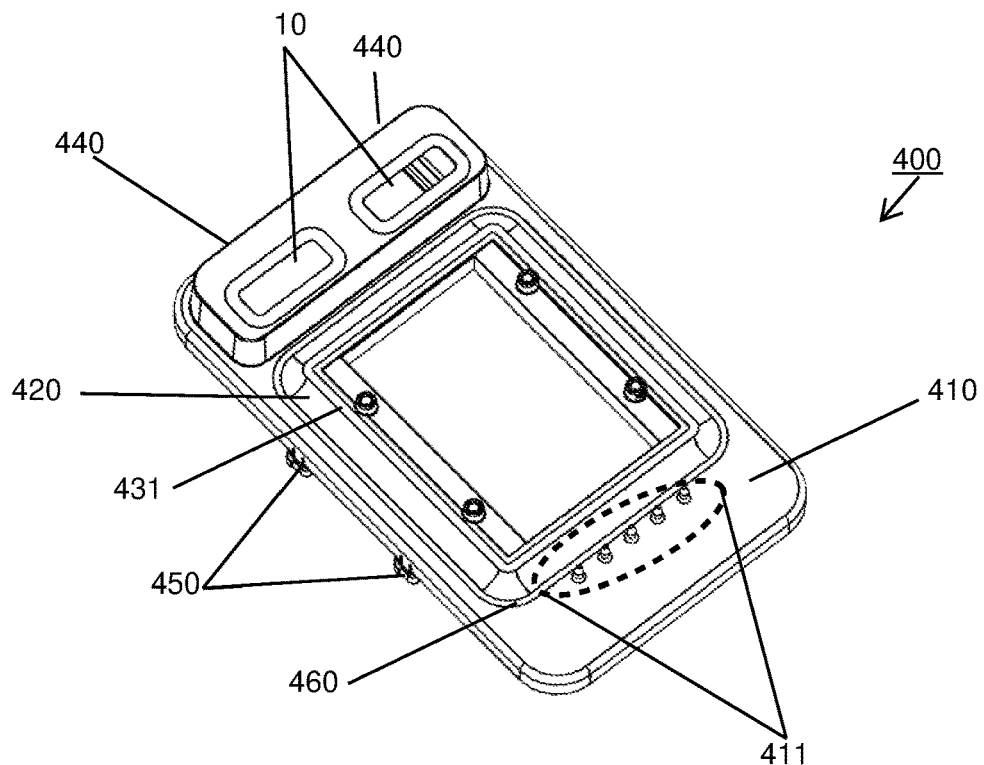
FIG. 4A is a top perspective view of a lid of a tissue culture vessel according to some exemplary embodiments of the invention.

FIG. 4A is a top perspective view, indicated generally as 400, of a lid of a tissue culture vessel according to some exemplary embodiments of the invention.

Figure 4B:
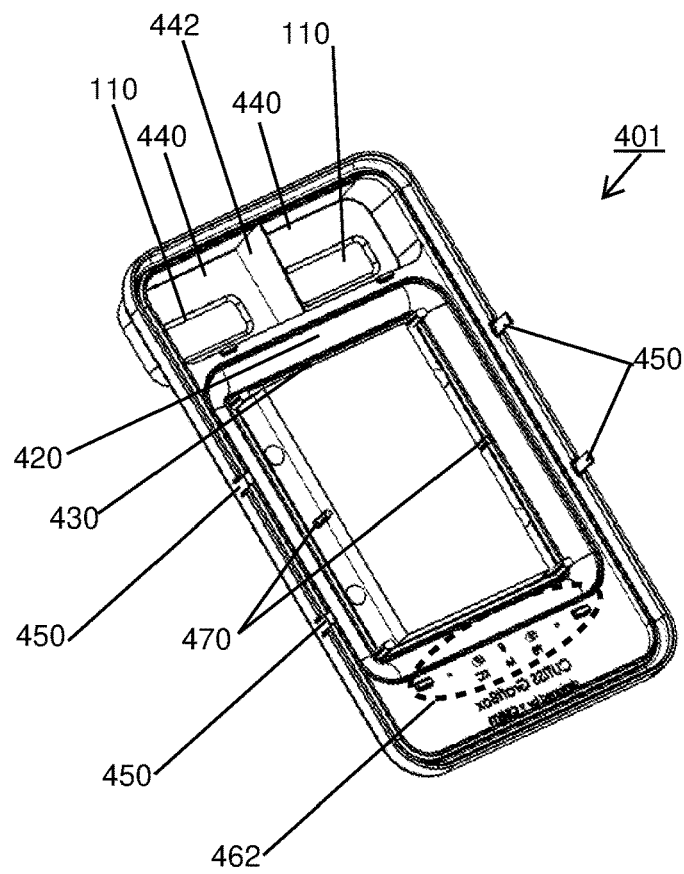
FIG. 4B is a bottom perspective view of the lid of a tissue culture vessel of FIG. 4A.

FIG. 4B is a bottom perspective view, indicated generally as 401, of the lid of a tissue culture vessel of FIG. 4A.

Depicted exemplary lid 400 includes a rigid frame 410 with a flexible bellows 420 deployed therein. Bellows 420 holds a plunger 431 in a fixed orientation with respect to frame 410. In some embodiments, plunger 431 is constructed of a transparent material (e.g. polycarbonate) to facilitate visual inspection of cells cultured in a graft support tray installed beneath lid 400.

In some exemplary embodiments of the invention, bellows 420 is normally open so that it holds plunger 431 in a raised position in the absence of an external force. According to various exemplary embodiments of the invention, the raised position is in a plane of frame 410 or higher. Alternatively or additionally, in some embodiments bellows 420 is manually removable (e.g. due to adhesive attachment) by an end user of the graft. In some embodiments a manually removable bellows contributes to ease of access to the graft for its removal from the vessel.

In the depicted embodiment, lid 400 includes one or more surge compartments 440 extending above a plane of an upper edge of frame 410. FIG. 4B shows a structural support 442 dividing surge compartment 440 into two compartments. In the depicted embodiment, surge compartments 440 are provided with gas permeable membranes 110 on an upper surface thereof. According to various exemplary embodiments of the invention attachment of gas permeable membranes 110 is from the inside or the outside. In some embodiments, gas permeable membranes 110 are provided as OXYPADS (Oxyphen GMBH, Switzerland). OXYPADS include a membrane center surrounded by adhesive edges which can be pressed onto a surface to seal the pad in place.

In the depicted embodiment, lid 400 includes snap hooks 450 on rigid frame 410 sized and positioned to engage a base covered by the lid.

In the depicted embodiment, lid 400 includes one or more external barbed connectors 460 (five are depicted but a smaller or larger number may be present) in fluid communication with internal outlet ports 462 (FIG. 4B). For example, barbed connectors 460 are connectable to supply tubing for $CO_2$/Air in and/or Fibroblasts (FB) and/or collagen gel (with or without cells contained therein) and/or Media and/or Keratinocytes (KC). In some embodiments one of barbed ports 460 is used for $CO_2$/Air out. Alternatively or additionally, in some embodiments, $CO_2$/Air leave the tissue culture vessel via the gas permeable membranes 110 of surge compartment 440. The arrangement of the barbed connectors 460 can either be next to each other or behind each other for a more efficient mass fabrication.

In some exemplary embodiments of the invention, lid 400 is fitted with an elastomeric seal (see 120 in FIG. 1) on a side of the lid which contacts a base when the vessel is assembled. According to these embodiments the seal forms an air and leak-tight connection to the base.

Exemplary Method

Figure 5:
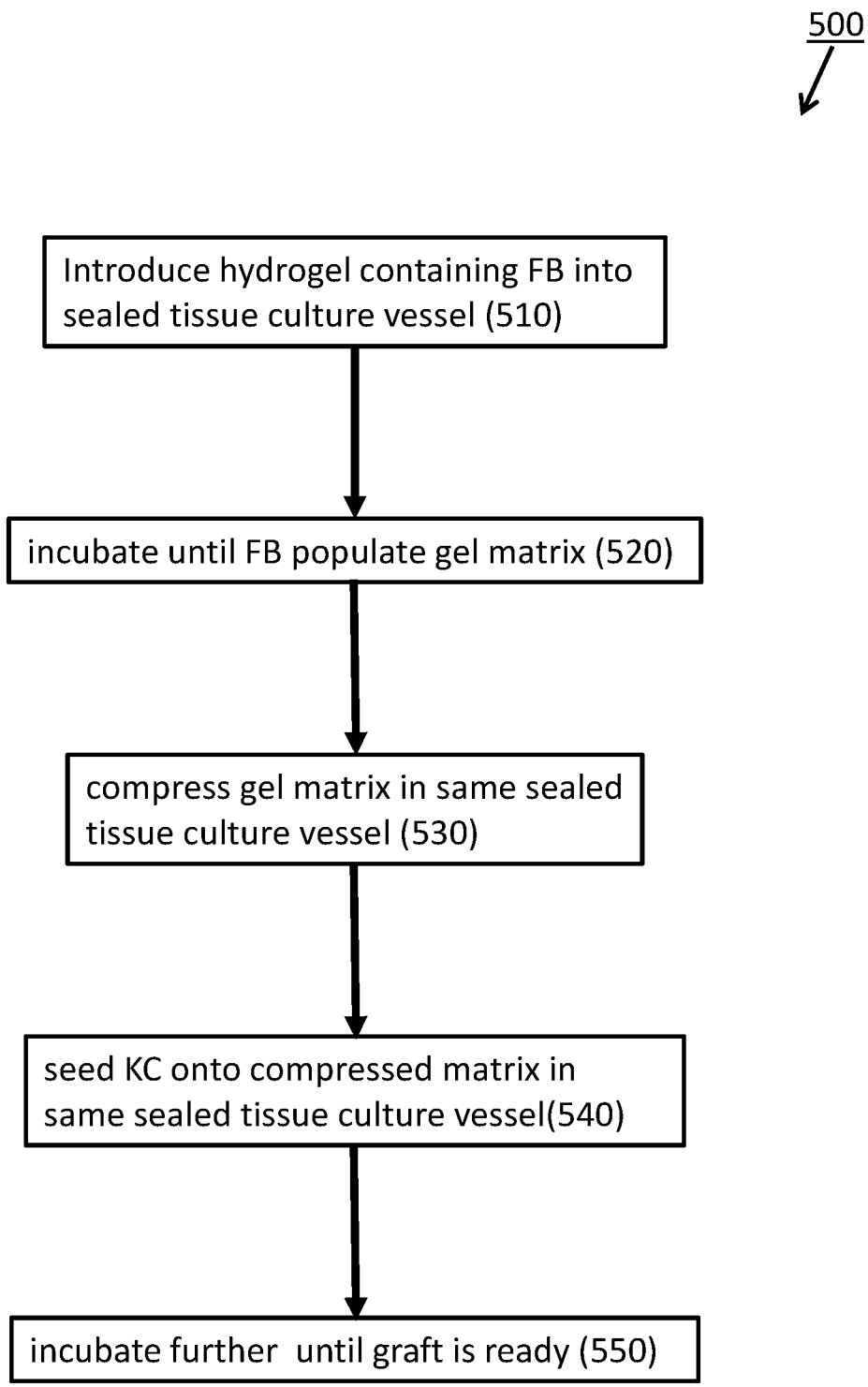
FIG. 5 is a simplified flow diagram of a graft preparation method according to some exemplary embodiments of the invention.

FIG. 5 is a simplified flow diagram of a graft preparation method, indicated generally as 500, according to some exemplary embodiments of the invention.

In the depicted embodiment, method 500 includes introducing 510 hydrogel containing fibroblasts (FB) into a sealed tissue culture vessel. After the hydrogel containing fibroblasts is introduced, the gel "polymerizes" (cross-linking due to addition of buffer in the cell culture media).

In the depicted embodiment, FB are then incubated 520 until the FB populate the gel matrix (typically after cross linking). Once the FB populate the gel matrix, the matrix is compressed 530 in the same sealed tissue culture vessel.

In some exemplary embodiments of the invention, after compression, the gel is left to incubate for a number of days (typically 5) so the cells can attach, populate and remodel the gel. In some embodiments the cell culture media is changed every 2 days.

In the depicted embodiment, keratinocytes (KC) are then seeded 540 onto the compressed matrix in the same sealed tissue culture vessel and incubated 550 further until the graft is ready. In some embodiments the graft is deemed ready for transplantation when a fibroblast rich dermal layer and a continuous keratinocyte/epidermal layer have formed. Alternatively or additionally, in some embodiments media change/removal during the culture of the skin is conducted during incubation 520 and/or 550 (e.g. using surge compartments 441). In some embodiments exchanging comprises: tilting the sealed tissue culture vessels in one direction to cause media to flow into a surge compartment; and tilting the sealed tissue culture vessels in a second direction to remove the media via gravitational flow to a waste container. As with any media change, the result is introduction of fresh nutrients for the cells and/or removal of metabolic waste.

Alternatively or additionally, in some embodiments the sample port is used to withdraw samples of the cell culture media. In some embodiments measurement of lactate and/or glucose and/or other metabolites permits assessment of cell growth and determination of readiness for transplant. Alternatively or additionally, sampling of the cell culture media via the sample port allows measurement of the microbiological load on the culture (e.g. sterility, mycoplasma, endotoxins etc.).

In some embodiments visual monitoring of growth of the FB and/or the KC within the tissue culture vessel using a microscope is conducted. According to various exemplary embodiments of the invention visual monitoring is conducted, for example at 520 and/or 550 and/or during 510 and/or 540.

In some exemplary embodiments of the invention, method 500 includes providing hydrogel, FB and KC to a plurality of the closed tissue culture vessels using a controller 830 (FIG. 8) and a pump 832 using a common set of reagent reservoirs (e.g. 810; 812; 814 and 816).

Additional Exemplary Method

Figure 6:
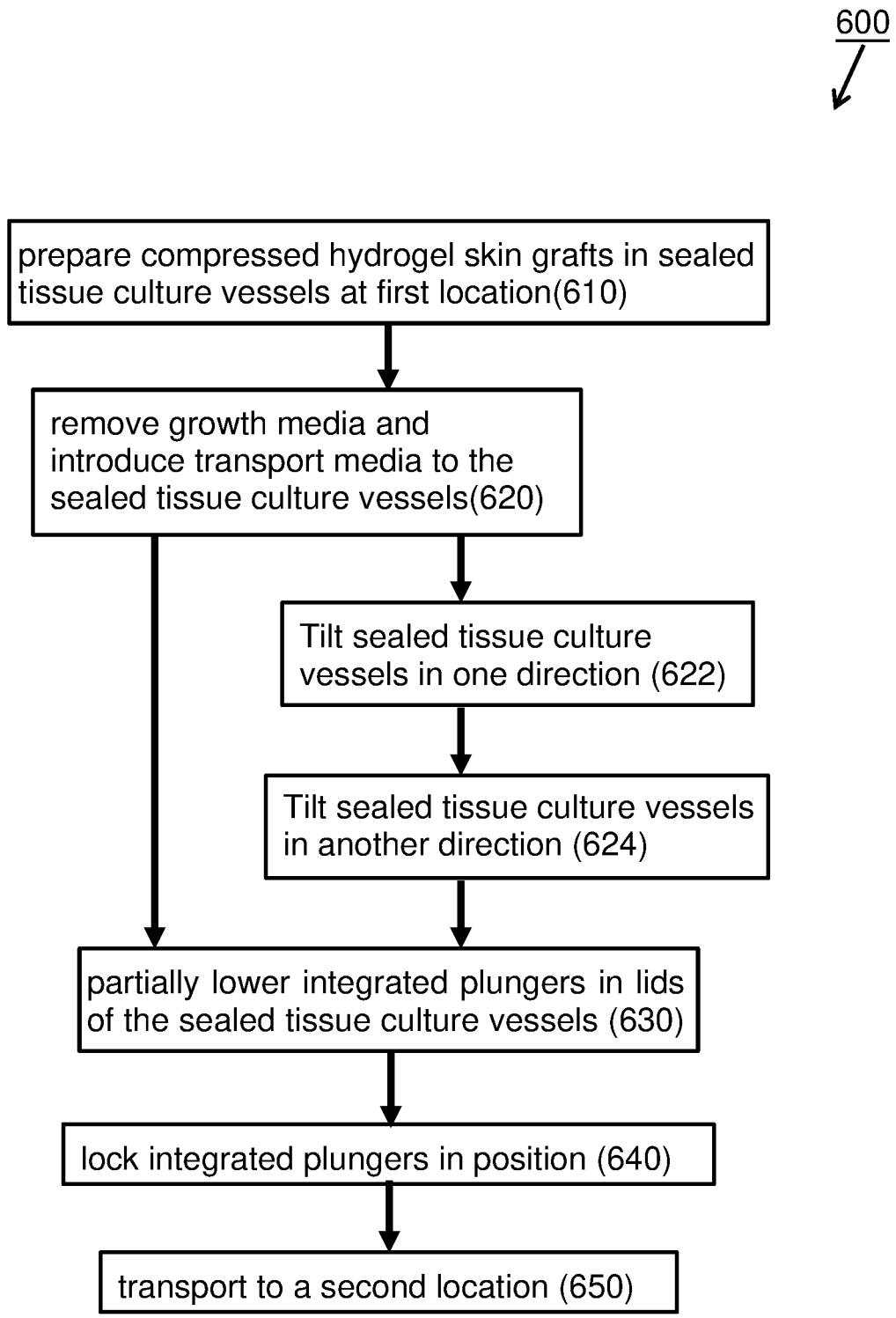
FIG. 6 is a simplified flow diagram of a graft production method according to additional exemplary embodiments of the invention.

FIG. 6 is a simplified flow diagram of a graft production method, indicated generally as 600, according to additional exemplary embodiments of the invention.

Depicted exemplary method 600 includes preparing 610 compressed hydrogel skin grafts in sealed tissue culture vessels at a first location (e.g. as described in the context of FIG. 5). Depicted exemplary method 600 includes removing 620 growth media and introducing transport media to the sealed tissue culture vessels and partially lowering 630 integrated plungers in lids of the sealed tissue culture vessels and locking 640 the plungers in position; and prior to transporting 650 to a second location. In some embodiments locking 640 contributes to an ability to securely hold the graft in position.

In the depicted embodiment, removing 620 includes tilting 622 the sealed tissue culture vessels in one direction to cause media to flow into a surge compartment and tilting 624 the sealed tissue culture vessels in a second direction to remove the media via gravitational flow to a waste container.

Exemplary Transport Lock

Figure 7A:
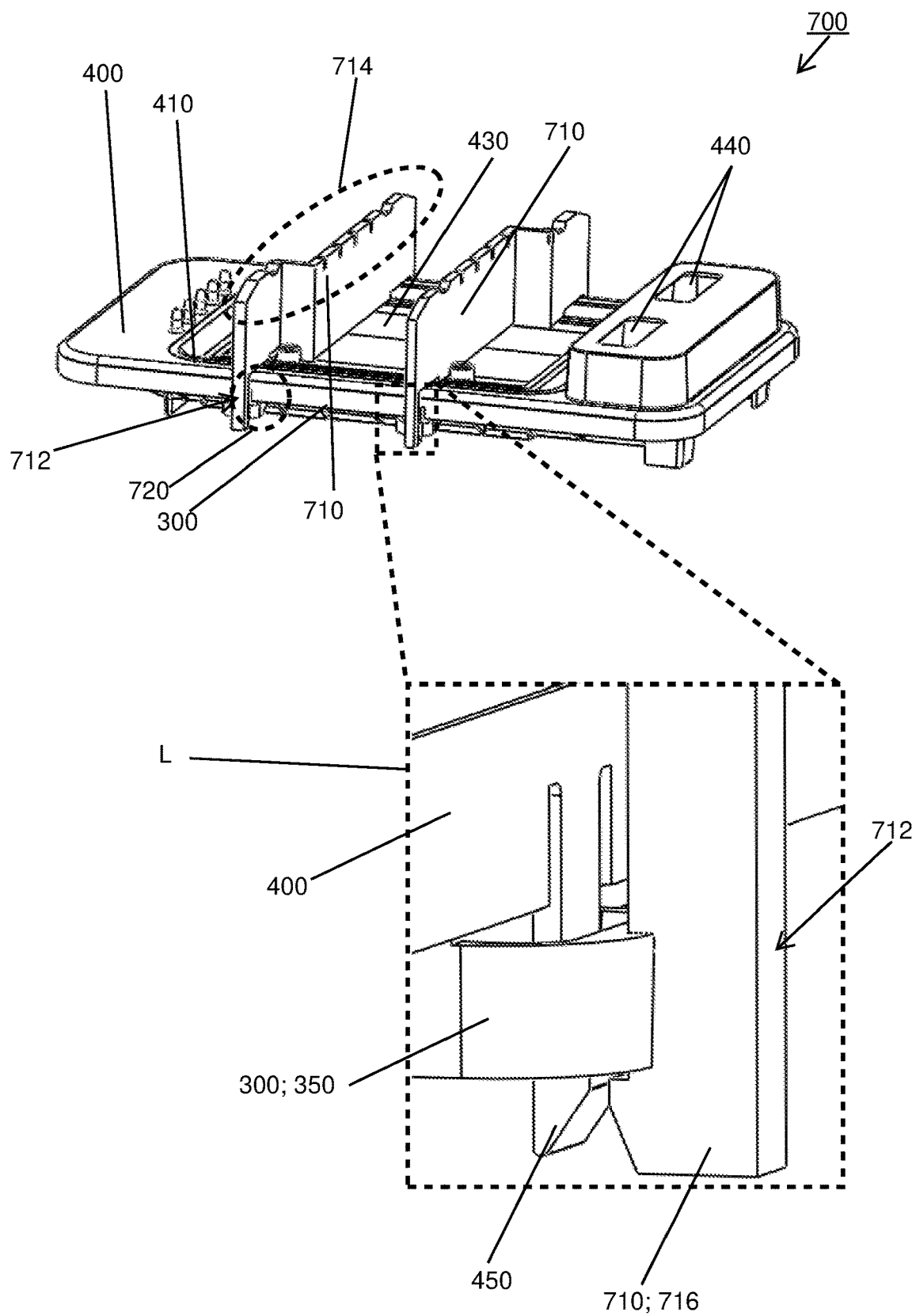
FIG. 7A is a perspective view of a tissue culture vessel fitted with two transport locks according to an exemplary embodiment of the invention including an inset "L" depicting the locking mechanism in detail.

FIG. 7A is a perspective view, indicated generally as 700, of a tissue culture vessel fitted with two transport locks 710 according to an exemplary embodiment of the invention. Inset L provides a close-up view of a connector 716.

Figure 7B:
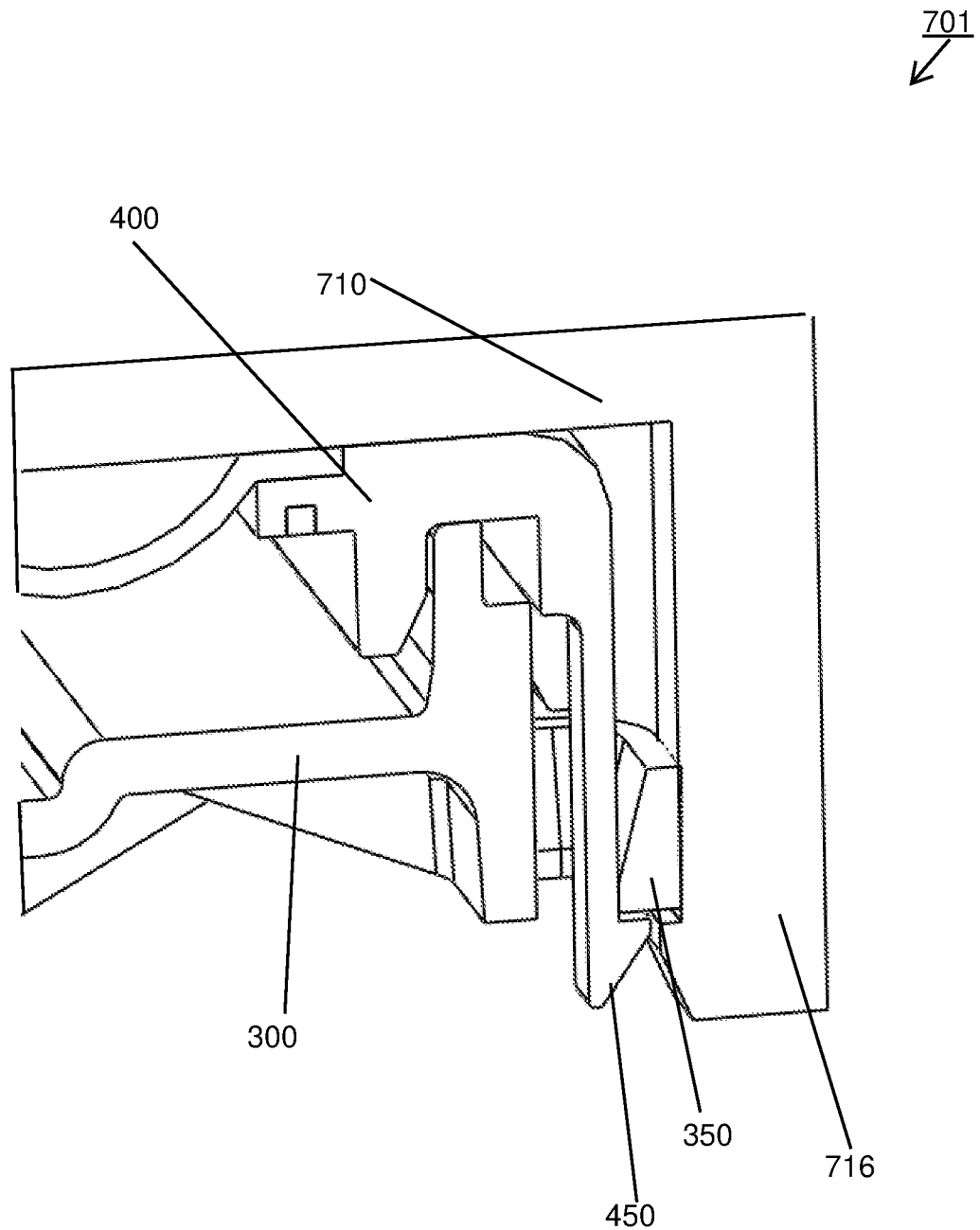
FIG. 7B is a transverse cross section of the juncture between a lid and a base of a tissue culture vessel and a transport lock according to an exemplary embodiment of the invention.

FIG. 7B is a transverse cross section, indicated generally as 701, of the juncture between a lid 400 and a base 300 of a tissue culture vessel and a transport lock 710 according to an exemplary embodiment of the invention.

In the depicted embodiment, the transport lock includes a spanning member 710 sized to conform to dimensions of the tissue culture vessel 100 (FIG. 1A). The transport lock has on its lower edge two notches 720 configured to conform to a profile of a frame 410 of lid 400 and a downward extension 712 between notches 720 and a clasp 716 sized to engage and retain a snap to fit connector 350 on base 300 on an outward edge of each of said notches. When the transport lock is in use, downward extension 712 and clasps 716 act in concert to hold tray 200 in its second operational state as described hereinabove. Alternatively or additionally, in some embodiments clasp 716 are "snap to fit" and constructed of flexible plastic so they can be disengaged manually In the depicted embodiment, the transport lock includes a series of slots (714) on an upper edge of spanning member 710. In some embodiments slots 714 are sized and positioned to engage and retain corresponding ribs 352 (see FIG. 3B) on a lower surface of a base 300 of a second tissue culture vessel 100 positioned above the transport lock.

Figure 7C:
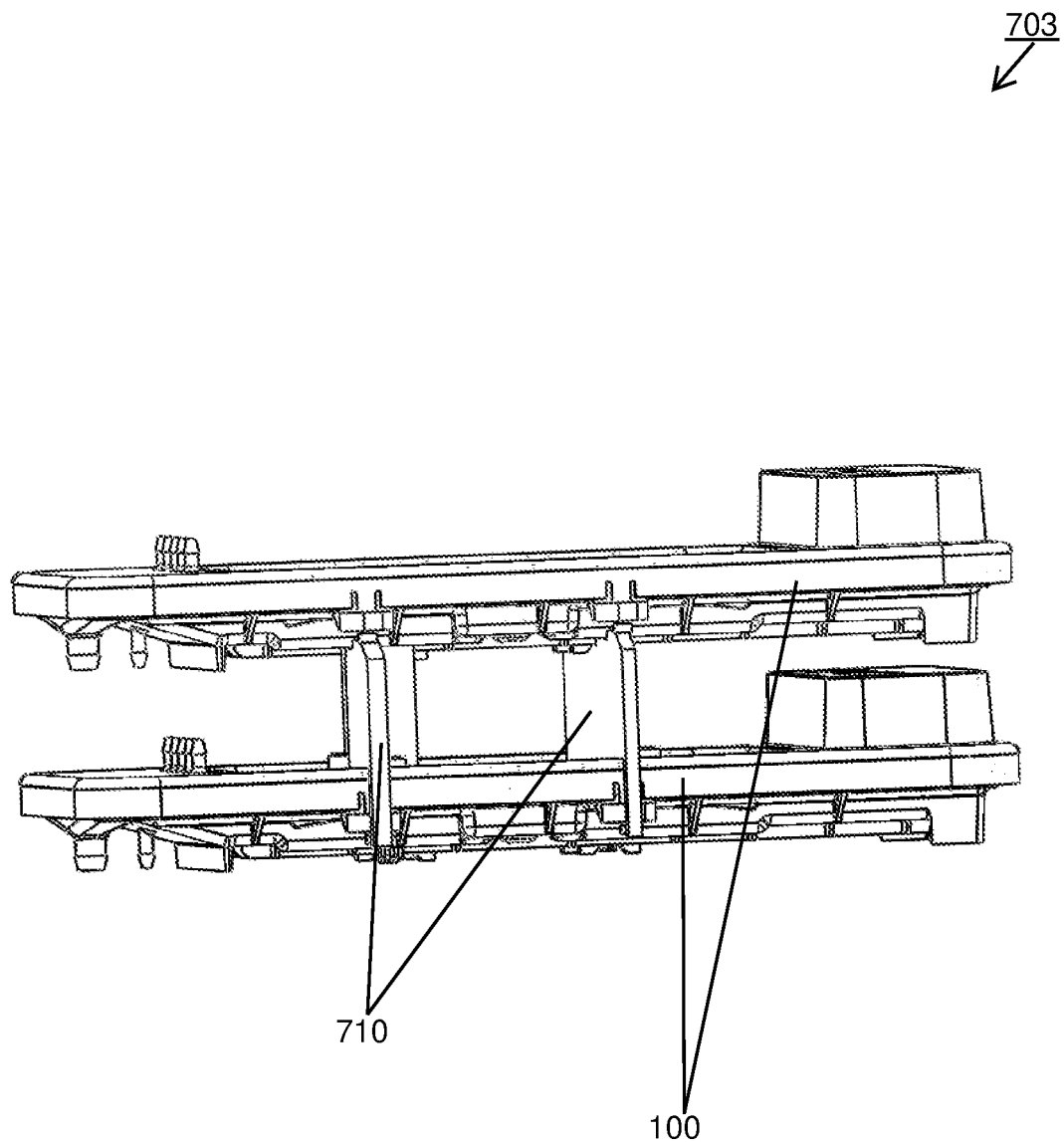
FIG. 7C is a side view of two tissue culture vessels assembled with two transport locks according to an exemplary embodiment of the invention.

FIG. 7C is a side view, indicated generally as 703, of two tissue culture vessels 100 assembled with two transport locks 710 according to an exemplary embodiment of the invention. The depicted exemplary assembly includes a plurality culture (two are depicted for clarity but a larger number would typically be present in actual practice) vessels 100 arranged in a vertical array with transport locks as described above interspersed between them.

Exemplary Measurements and Materials

In some embodiments tissue culture vessel 100 is sized to hold 160 to 170 ml of culture media.

In some embodiments, graft support tray 200 has a height of 5 to 15 mm (e.g. 10 mm), a width of 110 to 120 mm (e.g. 115 mm) and a length of 170 mm to 180 mm (e.g. 175.4 mm). A graft support tray of this size weighs 30-35 grams (e.g. 32.1 g) when constructed of polystyrene such as Ineos Styrolution PS 158N/L. In some embodiments, the membrane floor of the tray is made of Oxyphen Unique-Mem Track Etched Membrane corona treated, 51.9069.101.111, Polyester (PET), thickness 12 μm, pore size 3.0 μm, and pore density $0.6e^6/cm^2$. In some embodiments, tray 200 is produced by injection molding with subsequent heat boding of the membrane.

In some embodiments, lid 400 has a height of 35 to 45 mm (e.g. 40.5 mm), a width of 155 to 165 mm (e.g. 158 mm) and a length of 255 to 265 mm (e.g. 259.3 mm). In some embodiments, the rigid portions are constructed of polycarbonate such as Trinseo Calibre Megarad 2081-15 Polycarbonate and flexible bellows 420 is constructed of a thermoplastic elastomer such as Kraiburg TPE Thermolast M TM5ADT (50Sh). In some embodiments, lid 400 is produced by injection molding with subsequent over molding and drilling of ports.

In some embodiments, base 300 has a height of 20 to 30 mm (e.g. 24 mm), a width of 160 to 165 mm (e.g. 162.3 mm) and a length of 250 to 255 mm (e.g. 253.6 mm). A box of this size weighs 200 to 204 grams (e.g. 202 grams) when constructed of polycarbonate, such as Trinseo Calibre Megarad 2081-15 Polycarbonate. In some embodiments, base 300 is produced by injection molding with subsequent drilling of ports.

Exemplary Operational Considerations

In order to empty media from vessel 100, the vessel is first tilted along the transverse axis backwards (away) from the waste drainage port 344 to remove media from the top compartment into the surge compartments 440. Once the media accumulates in surge compartments 440, vessel 100 tilted towards waste drainage port 344 at an angle of ≤20°. Port 344 is connected to a waste receptacle and opened. With an angle of 20° less than 10% of media is retained in vessel 100. By returning vessel 100 to the neutral position port 344 rises above liquid level and fresh media can be introduced via one of ports 460 in lid 400.

For seeding of KC (keratinocytes), the vessel is first tilted along the transversal axis backwards (away) from the waste drainage port 344 to remove liquid from the top compartment into the surge compartments 440, at an angle of 26°. With an angle of 26°, only 4 ml of media is retained in tray 200. After returning vessel 100 to the neutral position KC can be seeded via one of ports 460 in lid 400.

A vessel 100 with dimensions as described above holds 165 ml±10% of media which is sufficient to ensure a 4 mm immersion of a graft growing in support tray 200. Roughly 40 ml of media is present in graft support tray 200. The remaining volume is inside base 300 but outside and/or below tray 200.

During introduction of hydrogel into graft support tray 200, membrane floor 220 should be raised above support surface 310 of base 300. First springs 230 on support tray 200 ensure that this is the case. After a first incubation (which allows the hydrogel to cross-link), the gel is compressed. In order to facilitate compression, the membrane has to touch support surface 310 of base 300 to allow wetting and/or to allow counter pressure support (like tent fabrics where it starts to leak where you touch). After the compression, support tray 200 is returned to its initial position by springs 230 and/or 232. The space underneath support tray 200 is sufficient for the amount of media required for the cell growth of the graft. In some embodiments liquid permeable membrane floor 220 allows nutrients from media in the space under tray 200 to nourish cells growing in and/or on hydrogel in the tray.

Exemplary Graft Culture System

Figure 8A:
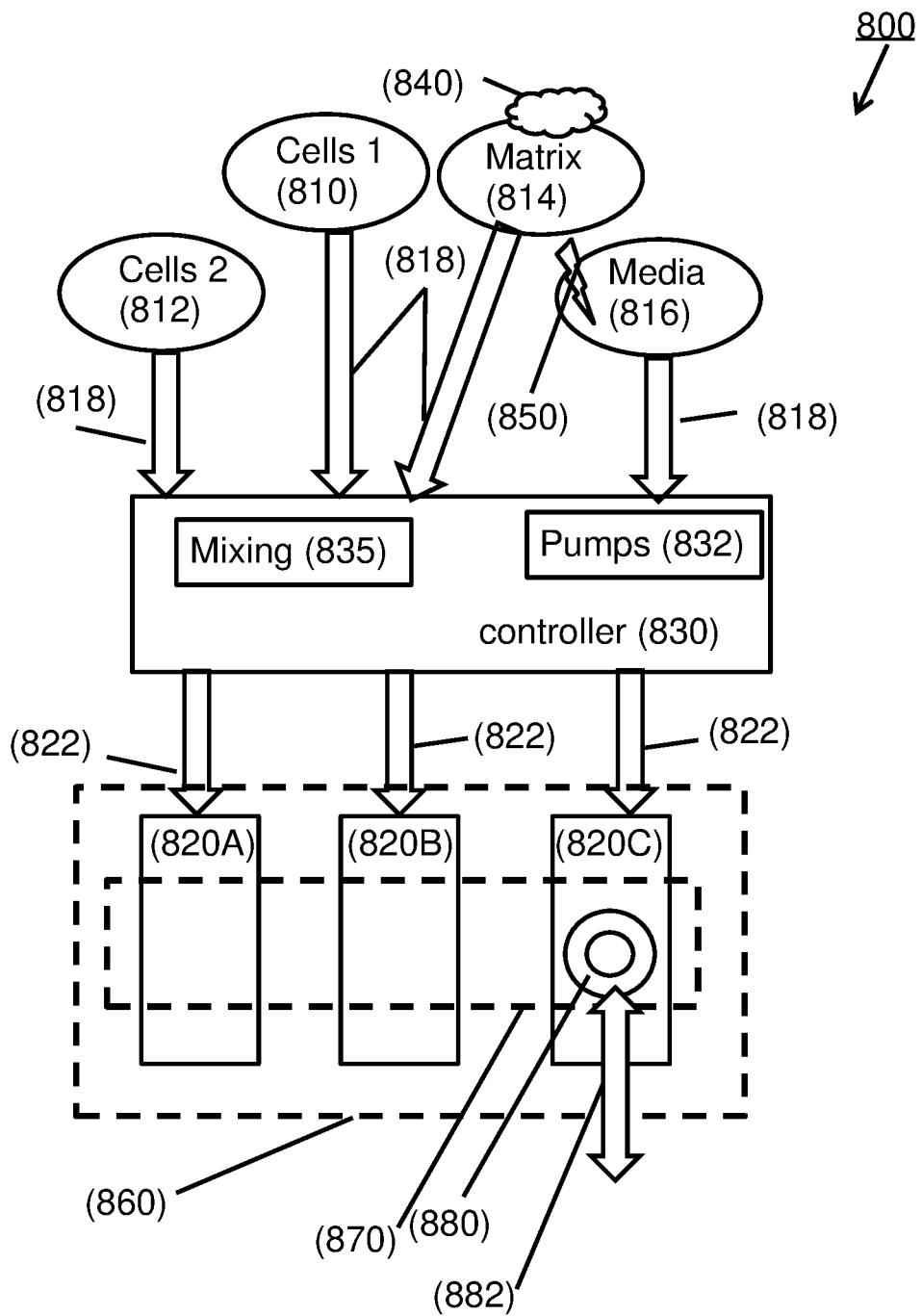
FIG. 8A is a simplified schematic representation of a graft culture system according to an exemplary embodiment of the invention.

FIG. 8A is a simplified schematic representation of a graft culture system, indicated generally as 800, according to an exemplary embodiment of the invention.

Figure 8B:
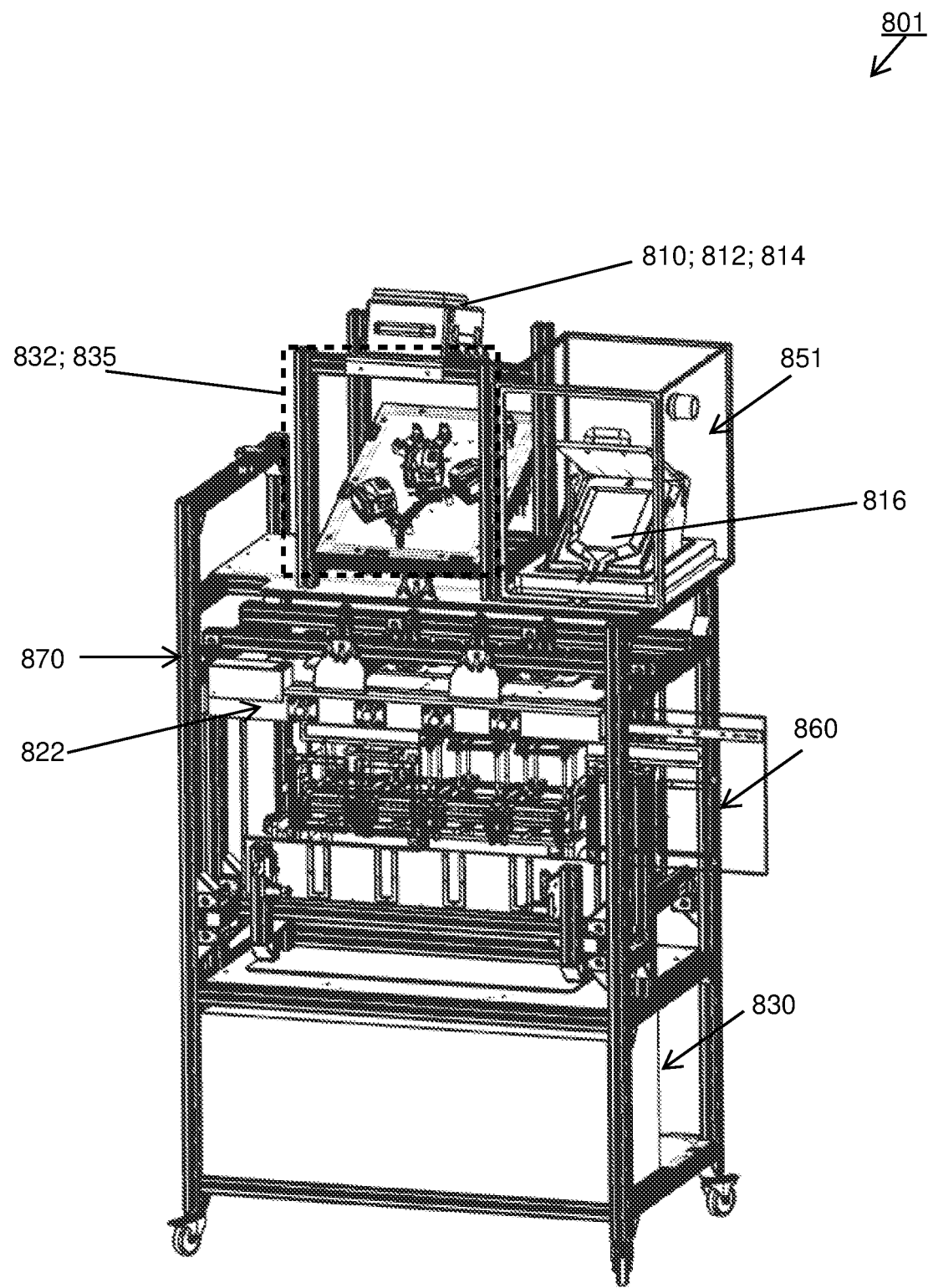
FIG. 8B is a front view of a graft culture system according to an exemplary embodiment of the invention.

FIG. 8B is a front view of a graft culture system, indicated generally as 801, according to an exemplary embodiment of the invention.

In the depicted embodiment, the system (800) includes a plurality of graft culture containers (820A; 820B; 820C) and reservoirs for cell suspension(s) (810; 812), gel matrix material (814) and culture media (816). In the depicted embodiment, conduits (818; 822) connect each of reservoirs (810; 812; 814 and 816) to each of the culture containers (820A; 820B; 820C). While three culture containers are depicted for clarity, a much larger number is actually present in many embodiments of the invention. Depicted exemplary system 800 includes a controller (830) configured to deliver the cell suspension(s), gel matrix material and culture media through the conduits to the culture containers in a coordinated manner to produce grafts. In some exemplary embodiments of the invention, the reservoirs for cell suspensions include at least one fibroblast (FB) reservoir (810) and at least one keratinocyte (KC) reservoir (812).

According to various exemplary embodiments of the invention the reservoirs for cell suspensions include at least two reservoirs for at least two different cell types selected from the group consisting of fibroblasts (FB), keratinocytes (KC), adipocytes, myocytes, neuronal cells, pericytes, stem cells, and Induced Pluripotent Cells (IPCs). According to various exemplary embodiments of the invention the stem cells include epithelial stem cells and/or mesenchymal stem cells. In some exemplary embodiments of the invention, use of multiple cell types contributes to an ability to generate tissue (soft and/or hard) and/or organs.

In some embodiments, the reservoirs for cell suspensions include at least two reservoirs for at least a first cell type of epithelial origin and a second cell type selected from the group consisting of cells of mesenchymal cells, cells of dermal origin, adipocytes, myocytes, neuronal cells, pericytes and stem cells.

In some exemplary embodiments of the invention, system 800 includes valves (see, for example 2910 in FIG. 8D) in the conduits under control of controller 830. In FIG. 8D, 2930 is a support structure for conduits not in use.

Alternatively or additionally, in some embodiments reservoir for gel matrix 814 includes a cooling element 840. In some embodiments, cooling of the gel matrix prevents pre-mature gelation and/or contributes to flowability in conduits 818 and/or 822. In some exemplary embodiments of the invention, the cooling element 840 includes a Peltier cooling body. In the depicted embodiment, controller 830 includes pumps 832 to move the cell suspension(s), gel matrix material and culture media through conduits 818 and/or 822. In some embodiments, pumps 832 are external to controller 830. In the depicted embodiment, system 800 includes a heater 850 positioned to heat culture media in reservoir 816. In some exemplary embodiments of the invention, a common Peltier unit cools matrix material in reservoir 814 and heats media in reservoir 816.

In the depicted embodiment, system 800 includes a mixing module 835 that receives cells from one reservoir (e.g. 810) and gel matrix from a different reservoir (e.g. 814) and mixes cells into the matrix to produce a gel matrix cell suspension of cells. Referring now to FIG. 8K, in some embodiments, mixing module (835) mixes cells from one reservoir (e.g. 810) with buffer from a second reservoir (.g. 817) to produce a buffered cell suspension. In the depicted embodiment, this is accomplished using a static mixer 837. In the depicted embodiment, module 835 then mixes the buffered cell suspension with gel matrix from a third reservoir (e.g. 814) to produce a gel matrix cell suspension. In the depicted embodiment, this is accomplished using a static mixer 837.

In the depicted embodiment, system 800 includes an incubation chamber 860 designed and configured to contain the plurality of graft culture containers. In some embodiments, temperature and/or humidity and/or $CO_2$ concentration within chamber 860 are controlled by controller 830.

In the depicted embodiment, system 800 includes a compression mechanism 870 operable by controller 830 to compress a gel matrix in one or more of graft culture containers 100.

In the depicted embodiment, system 800 includes a camera 880 and bidirectional data communication link 882 to an external user input device. In some embodiments, the external user input device displays output pictures from camera 880 and includes a user interface (e.g. a graphical user interface (GUI)) for entry of commands to controller 830. In some exemplary embodiments of the invention, images output by camera 880 are used in assessment of color (indicator of pH change and associated nutritional value of the medium) and/or assessment of turbidity (indicative of presence of contaminants) of the culture medium. Alternatively or additionally, in some embodiments output by camera 880 are used in assessment of smoothness of surface of gel and/or to detect presence of gas bubbles as part of the assessment of quality of the tissue formation process.

Alternatively or additionally, in some embodiments controller 830 is adapted to periodically remove media from the graft culture containers (e.g. 820A; 820B and 820C) and add new media from one of the reservoirs (e.g. 816). In some exemplary embodiments of the invention, controller 830 is programed with a schedule. In some embodiments, controller 830 reverses a flow direction of pump 832 to withdraw media from the culture containers via conduits 822. In some exemplary embodiments of the invention, separate conduits are used for removal of spent media and for introduction of fresh media.

In some exemplary embodiments of the invention, each of the graft culture containers (e.g. 820A; 820B and 820C) is a tissue culture vessel 100 as described hereinabove. In some embodiments controller 830 tilts the culture containers 100 to prescribed angles to remove media as will be described in greater detail hereinbelow.

Figure 8C:
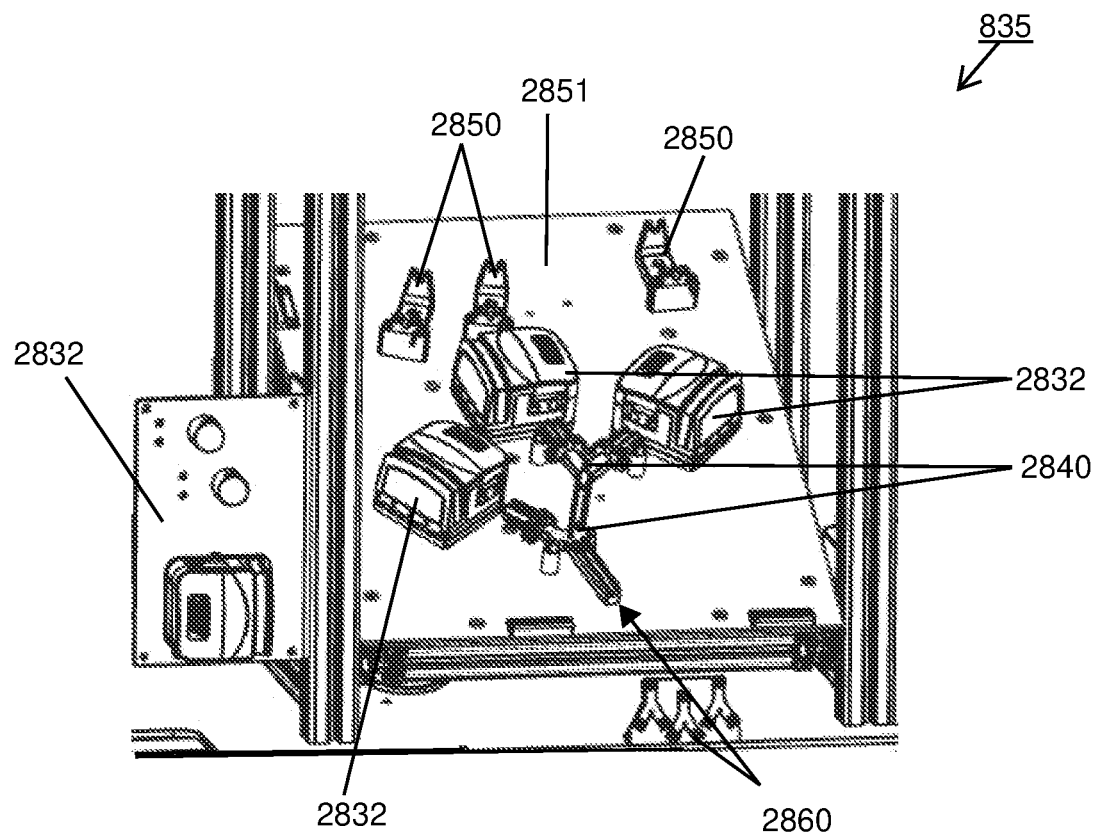
FIG. 8C is a front view of a mixing module according to some exemplary embodiments of the invention.
Figure 8D:
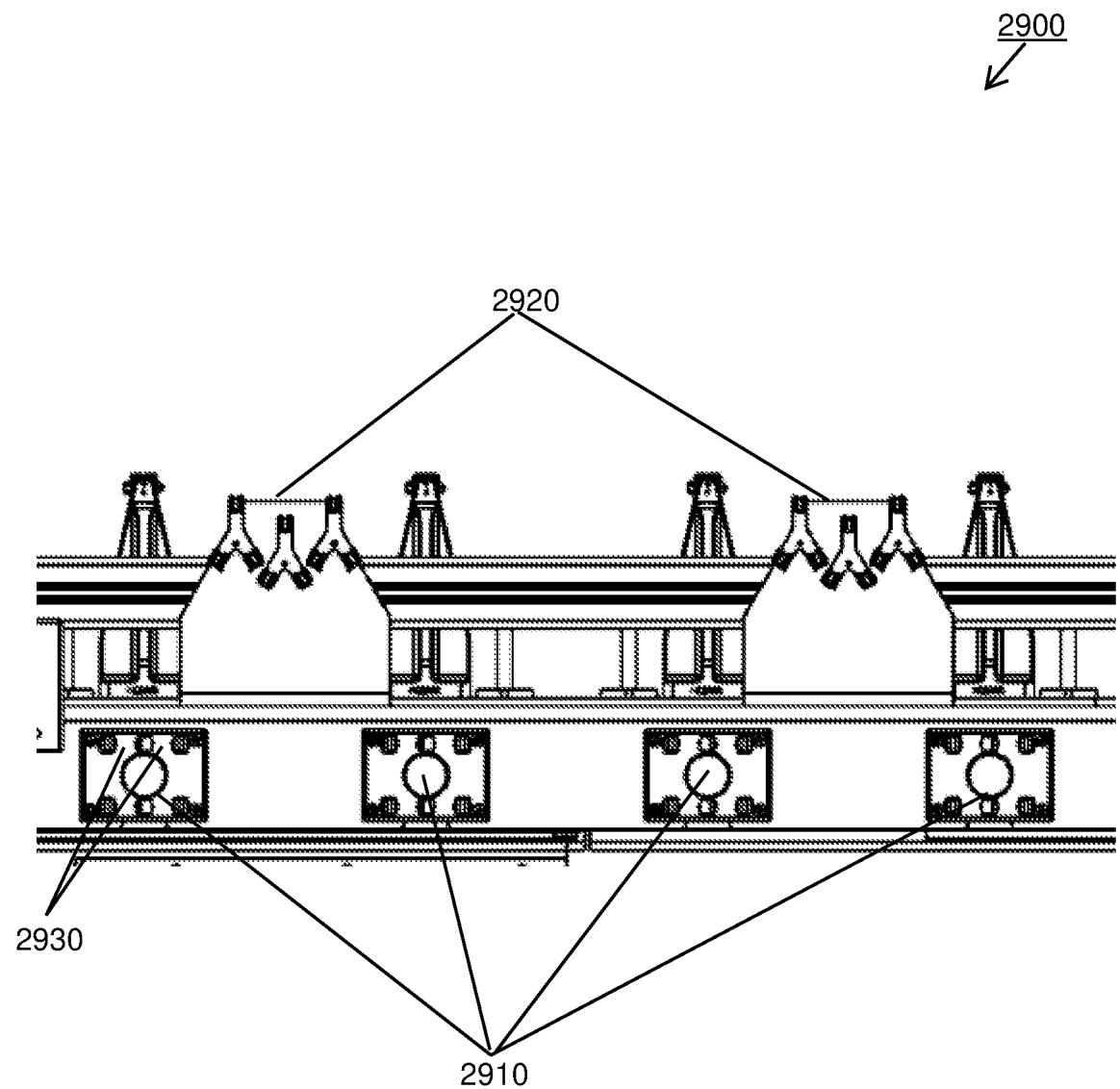
FIG. 8D is a front view of a dispensing module according to some exemplary embodiments of the invention.

FIG. 8C is a front view of a mixing module, indicated generally as 835 according to some exemplary embodiments of the invention FIG. 8C shows an exemplary embodiment of mixing module 835 in greater detail. In the depicted embodiment, mixing module 835 includes a static mixer employing a branched tubing strategy. In the depicted embodiment, mixing module 835 includes multiple peristaltic pumps 2832 (three are depicted as an example) secured on a support plate 2851 with an angle (such as 45°). In the depicted embodiment, fluid sensors 2840 are situated below and above the peristaltic pumps to allow control of liquid distribution. The depicted exemplary mixing module employs single use plastic tube kits, as is standard for closed system designs. The depicted exemplary configuration includes holding structures 2850 for aseptic connection points. In the depicted embodiment, additional holding structures for single or branching tube sets are included in the design 2860.

FIG. 8K is a simplified schematic representation of static mixers as employed in mixing module 835 of FIG. 8C according to some exemplary embodiments of the invention. In the depicted embodiment, mixers 837 receive liquids/suspensions from reservoirs 810; 814; 817 via conduits 818 and output mixtures via conduit 822. In the depicted embodiment, mixer 837 is a connector with two inputs and a single output. The two input flows mix due to turbulence created when they meet in mixer 837. In some embodiments, this configuration obviates a need for moving parts in the mixer.

FIG. 8D is a front view of a dispensing module, indicated generally as 2900, according to some exemplary embodiments of the invention. In some exemplary embodiments of the invention, the dispensing module employs single use tube trees for parallel dispensing of liquids. In the depicted exemplary embodiment of FIG. 8D, dispensing module 2900 includes holders 2920 for multiple branching tube trees. In some exemplary embodiments of the invention, holders 2920 contribute to an ability of liquid to flow evenly through the tubing and/or contributes to prevention of kink formation in the tubing which could cause blockage of flow. In the depicted embodiment, 2930 secures tubes not in use.

In the depicted embodiment, module 2900 has four solenoid valves 2910. This arrangement contributes to an ability to control liquid distribution. For example, if solenoid valves 2910 are triggered sequentially for 1 second each, uniform distribution of liquids is accomplished. In other exemplary embodiments of the invention, more valves are used for parallel liquid distribution to a greater number of containers.

Figure 8E:
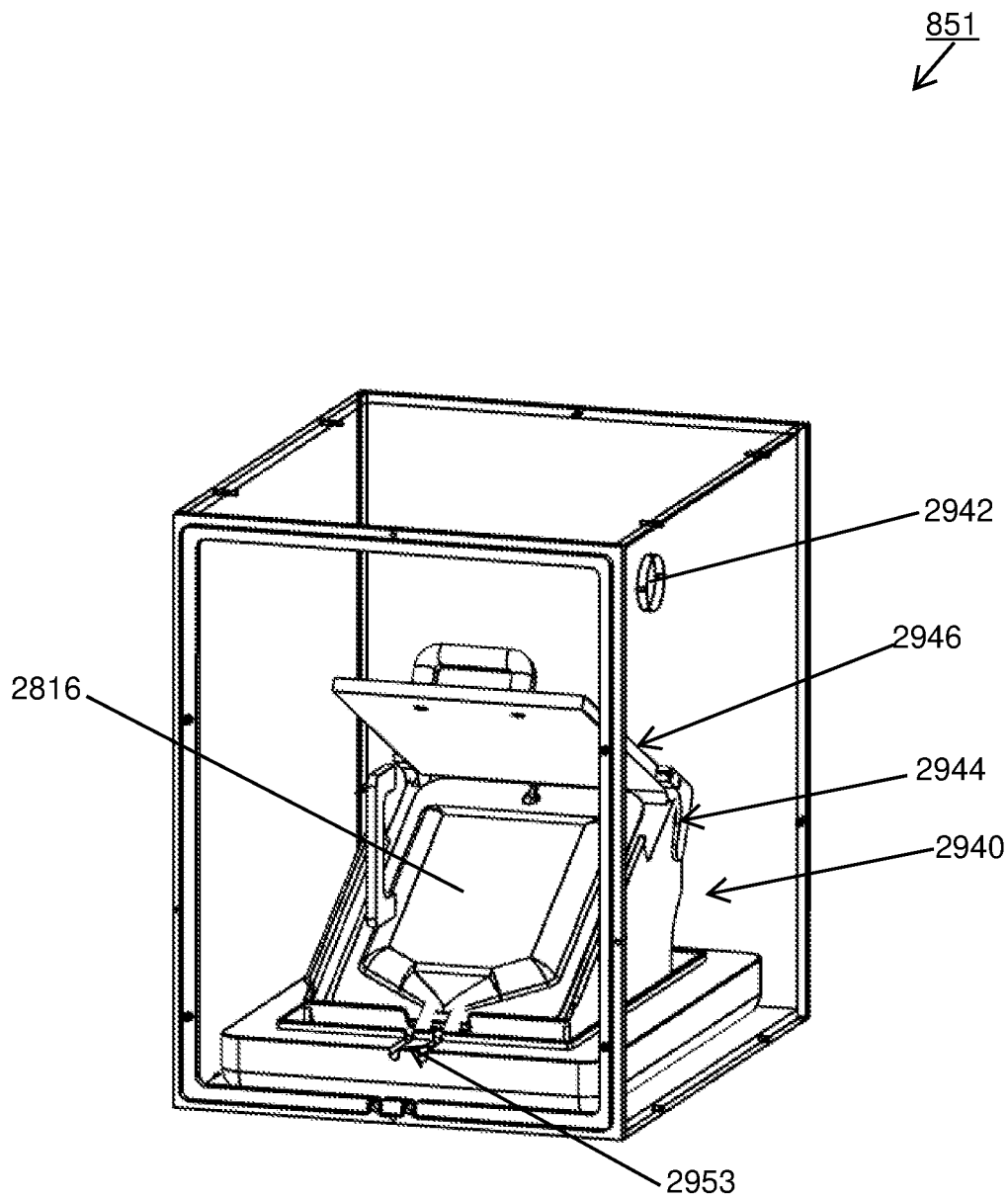
FIG. 8e is a front view of a media reservoir configured as a prewarming station for medium or other cell culture reagents according to an exemplary embodiment of the invention.

FIG. 8E is a front view of a media reservoir configured as a prewarming station, indicated generally as 851, for medium or other cell culture reagents according to an exemplary embodiment of the invention.

FIG. 8E depicts an exemplary media reservoir 816 (FIG. 8A) configured as a prewarming station 851 for medium or other cell culture reagents before dispensing to single use containers 100 as described hereinabove. Depicted exemplary station 851 is used in connection with disposable plastic tubing and bag system. For example, a tubing system that connects aseptically (e.g. ASEPTIQUICK) on one end to a plastic bag (medium reservoir 816 (FIG. 8A)) stored at room temperature (external storage hook on left side of device). The reservoir could also be stored in a cooled compartment. In the depicted embodiment, tubing that is connected on one side to a medium reservoir (816; FIG. 8A) is connected on the other side to a smaller medium bag 2816. Bag 2816 is filled when required with a specified amount of medium for prewarming. Bag 2816 has a second tubing outlet for the distribution of the prewarmed medium to containers 100.

In the depicted embodiment, chamber 2940 is filled with externally preheated air (to a desired temperature, such as 37° C.) via connection point 2942. In some exemplary embodiments of the invention, connection point 2942 is connected through large diameter tubing to an environmental control system such as the environmental control system "CUBE" by LIFE IMAGING SYSTEM or an incubator. In the depicted embodiment, chamber 2940 contains a storage unit 2944 into which medium bag 2816 is placed. The unit is shaped to support the bag, with a hook at the top to hold the bag. The storage unit 2944 has a lid 2946. In some embodiments, storage unit 2944 and lid 2946 include a Peltier element that heats medium bag 2816 to the required temperature. In some exemplary embodiments of the invention, use of a Peltier element partially or fully obviates a need to connect chamber 2940 to an environmental control system. In either case (with or without connection to an environmental control system) chamber 2940 is fitted with guides and exit ports 2953 for the incoming and outgoing tubing.

Figure 8F:
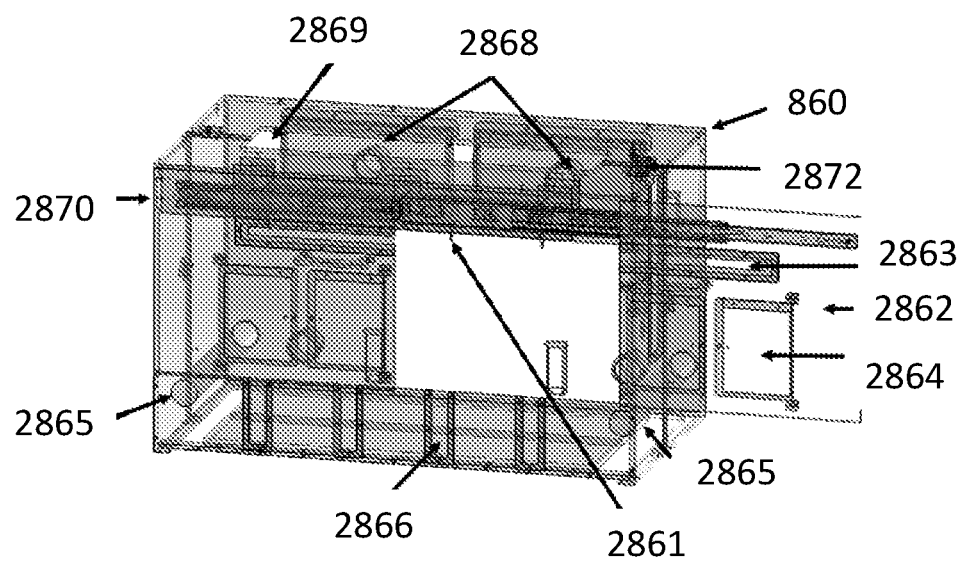
FIG. 8F is a front view of an incubation chamber according to an exemplary embodiment of the invention.

FIG. 8F is a front view of an incubation chamber, indicated generally as 860, according to an exemplary embodiment of the invention. In the depicted embodiment, single use graft culture containers 100 as described hereinabove are incubated in an incubation chamber 860. In some exemplary embodiments chamber 860 is adapted for compression of 3d matrices (hydrogels) and/or cultivation of the graft over a period of days or weeks. In some exemplary embodiments of the invention, part of the assembly of the 3D graft occurs outside chamber 860. In the depicted embodiment, chamber 860 has two sliding doors 2862 in the front for set up of containers 100. In the depicted embodiment, smaller doors 2864 are fitted for interactions during the process where temperature fluctuation in the chamber is not desired. In the depicted embodiment, the four smaller doors 2864 are fitted, however depending on the number of containers 100 the number of smaller doors 2864 could be increased. The sliding doors are fitted with slits 2863 lined with rubber to allow tubing to be connected from the outside of the environmental chamber with the inside. Similar rubber lined slits 2866 are fitted on the bottom of the device to allow tubing for waste disposal to exit the environmental chamber to connect to waste bags.

In some embodiments, incubation chamber 860 is filled with preheated air to produce an environment of a desired temperature (such as 37° C.). The air is preheated by an environmental control system such as the environmental control system "CUBE" by LIFE IMAGING SYSTEM or an incubator. In some embodiments, at heater air inlet ports 2868 are connected through large diameter tubing to an environmental control system. In the depicted embodiment, air return ports 2865 return air to the environmental control system through tubing.

In the depicted embodiment, opening 2869 provides an attachment interface for a compression module 1301 as described hereinbelow (see FIG. 8G and FIG. 13B and corresponding text). In the depicted embodiment, connection point 2861 facilitates attachment to a reservoir of $CO_2$ enriched, humidified air on one side and tubing connected to the culture container (e.g. 820A in FIG. 8A) on the other side.

A suitable environment for cell growth in culture containers 100 within chamber 860 requires air to be humidified and to contain 5% $CO_2$. In some exemplary embodiments of the invention, an air mixture containing 5% $CO_2$ is injected into the humidity chamber 2870. In some embodiments, the air mixture is provided by a system such as the "BRICK"

BY LIFE IMAGING SYSTEM or an incubator. In the depicted embodiment, water column 2872 ensures humidification of the air before distribution to the containers 100. In the depicted embodiment, 2861 serves as a connector port of humidity chamber 2870. In some embodiments, a culture container 100 is connected via tubing to connector 2861 to receive the air.

Figure 8G:
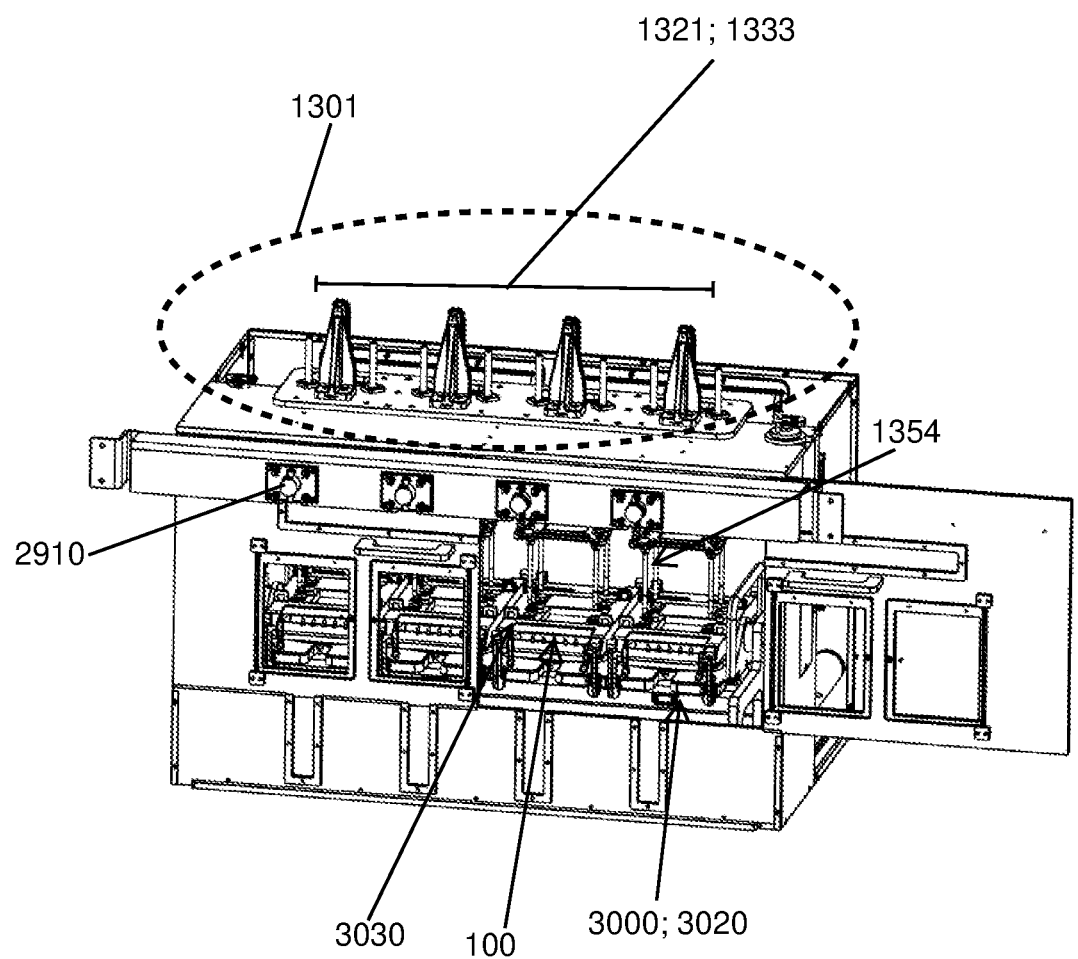
FIG. 8G is a front view of an incubation chamber as in FIG. 8F assembled with a compression module and tilt based media exchange mechanism according to an exemplary embodiment of the invention.
Figure 12A:
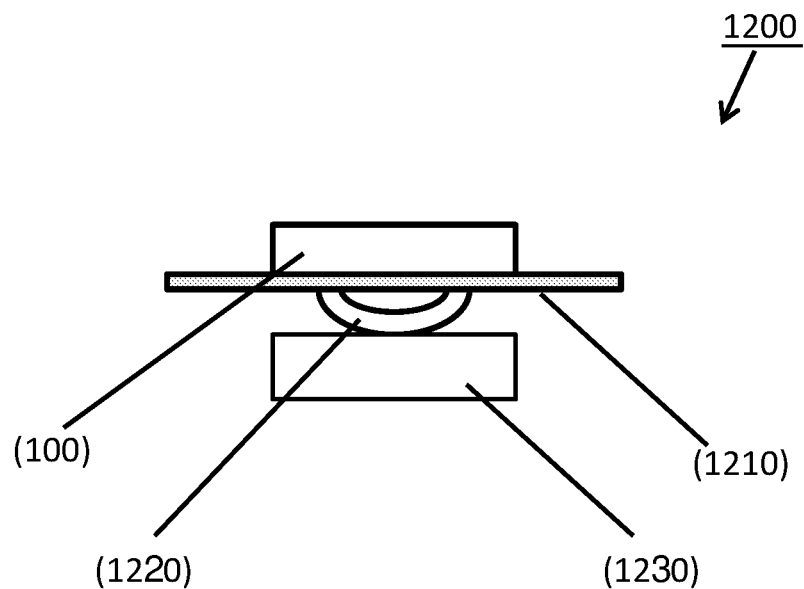
FIG. 12A is a simplified schematic representation of a tilt based media exchange system for cell culture according to an exemplary embodiment of the invention.
Figure 12B:
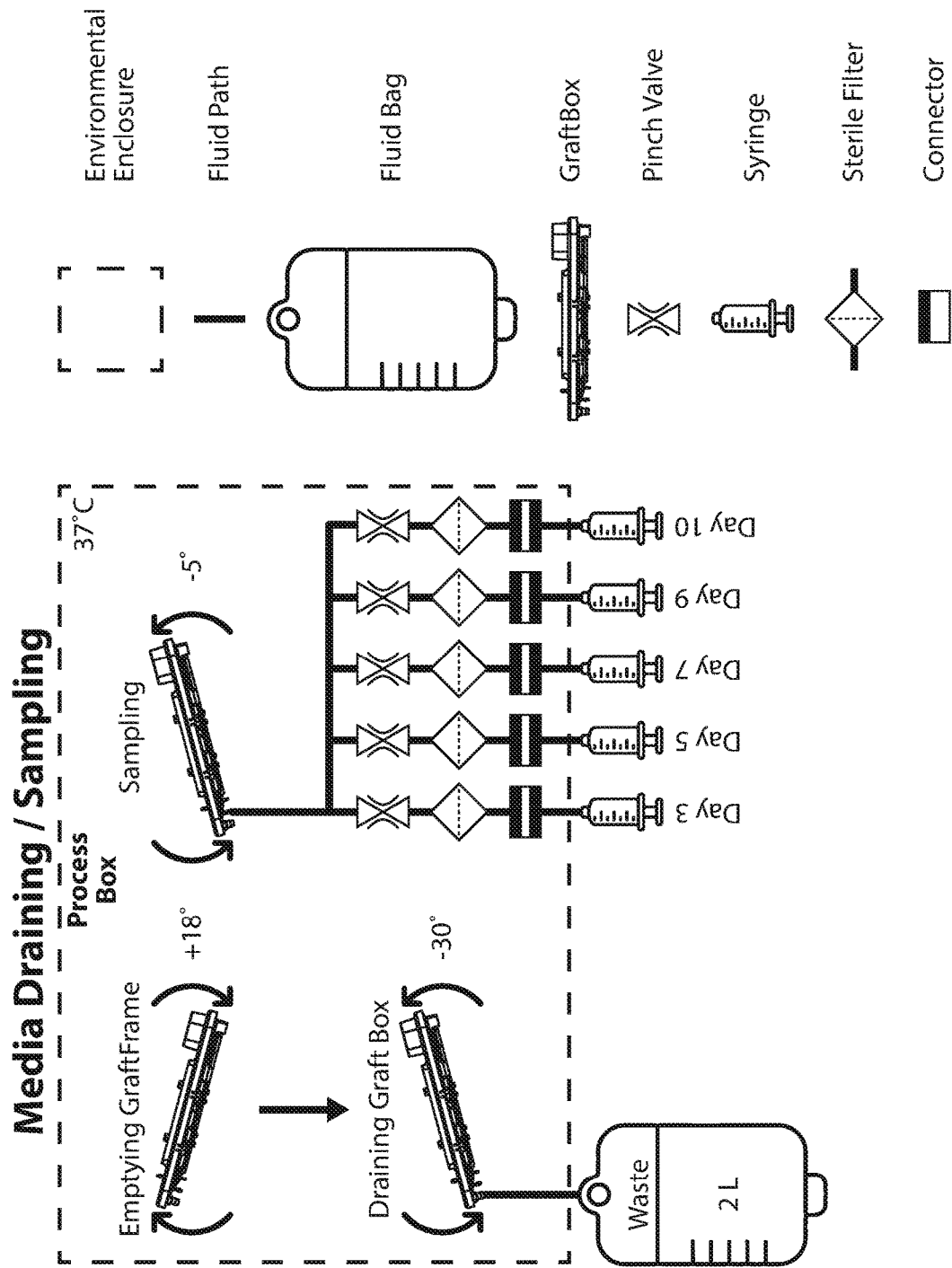
FIG. 12B is a simplified pictorial flow diagram of a tilt based media exchange system for cell culture according to an exemplary embodiment of the invention.

FIG. 8G is a front view of an incubation chamber as in FIG. 8F assembled with a compression module 1301 and tilt based media exchange mechanism 3000 according to an exemplary embodiment of the invention. In the depicted embodiment, incubation chamber 860 is assembled with a compression module 1301 as described below in the context of FIG. 13B. In the depicted embodiment, on the top front (outside) of chamber 860 valves 2910 are visible (see FIG. 8D and corresponding text). In the depicted embodiment, the compression system 1301 is inserted into incubation chamber 860 from above. In the depicted embodiment, a metal tilt table 3000 is positioned in chamber 860. Tilt table 3000 is tilted to allow media drainage from containers 100 as described below in the context of FIG. 8H; FIG. 12A and FIG. 12B. In the depicted embodiment, tilt table 3000 is driven by an actuator 3010 (See FIG. 8H). In some embodiments, tilt table 3000 is designed with a secondary function of heat storage. According to these embodiments, use of thick metal plates in construction of table 3000 creates a heat reservoir. In some exemplary embodiments of the invention, the heat reservoir contributes to consistency of temperature in chamber 860.

Figure 13A:
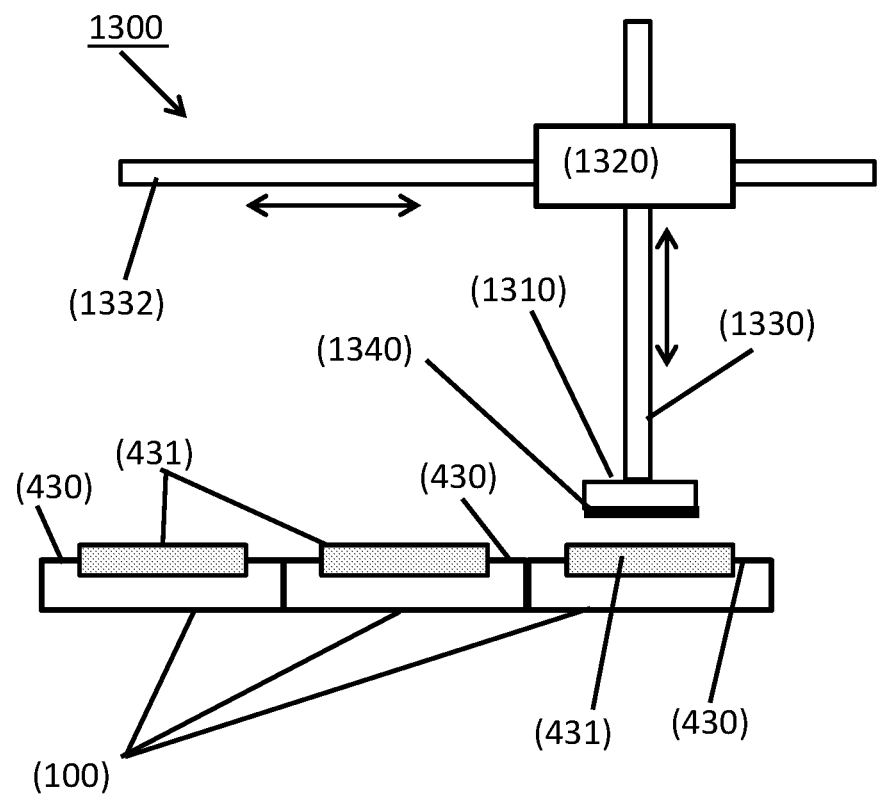
FIG. 13A is a simplified schematic representation of a compression module for a graft culture system according to an exemplary embodiment of the invention.
Figure 13B:
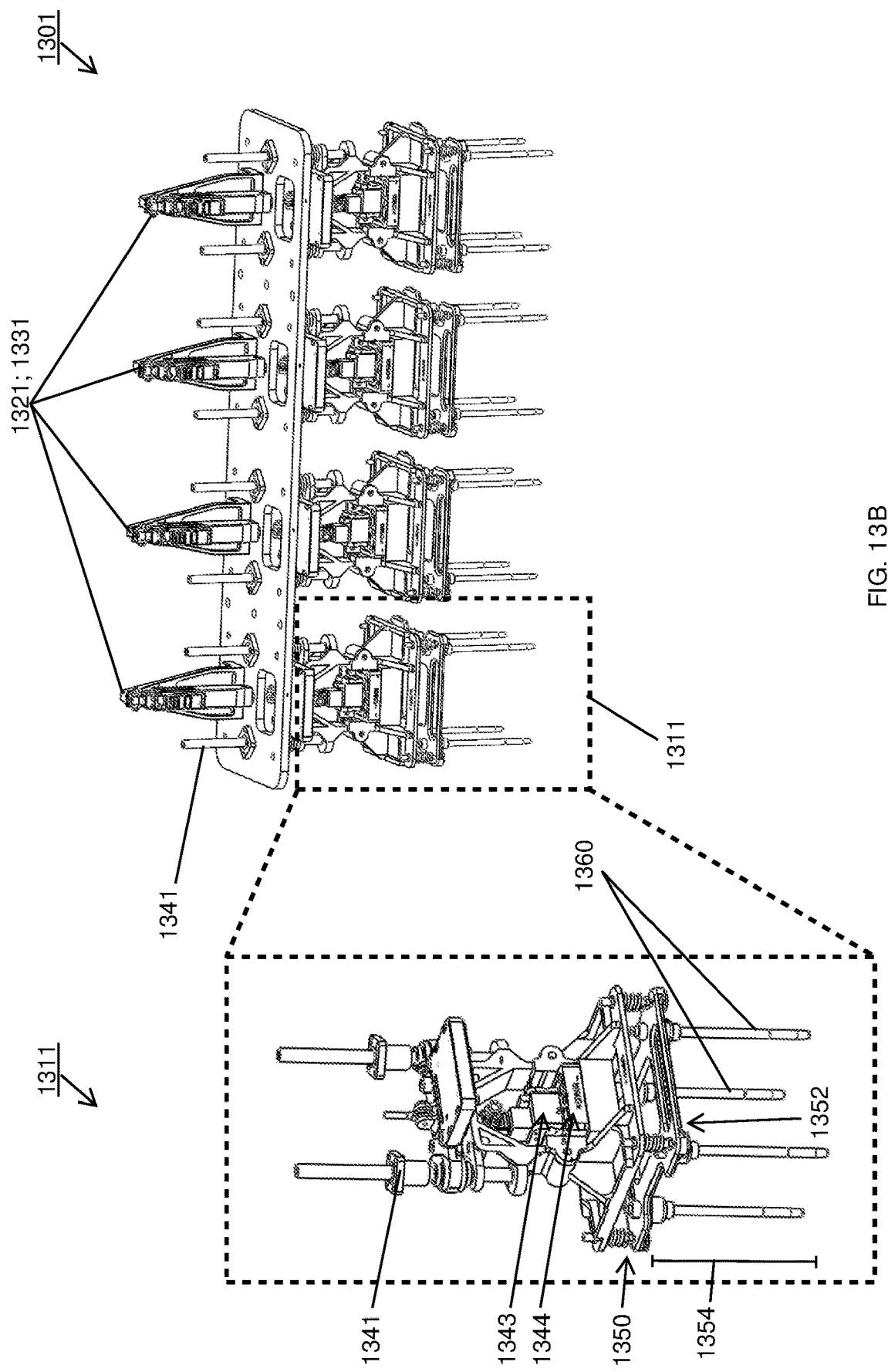
FIG. 13B is a front view of a compression module for a graft culture system according to an exemplary embodiment of the invention with an inset showing a piston assembly in isolation.

In the depicted embodiment, piston head 1354 is visible (See FIG. 13B and accompanying text for description of piston head function).

Figure 8H:
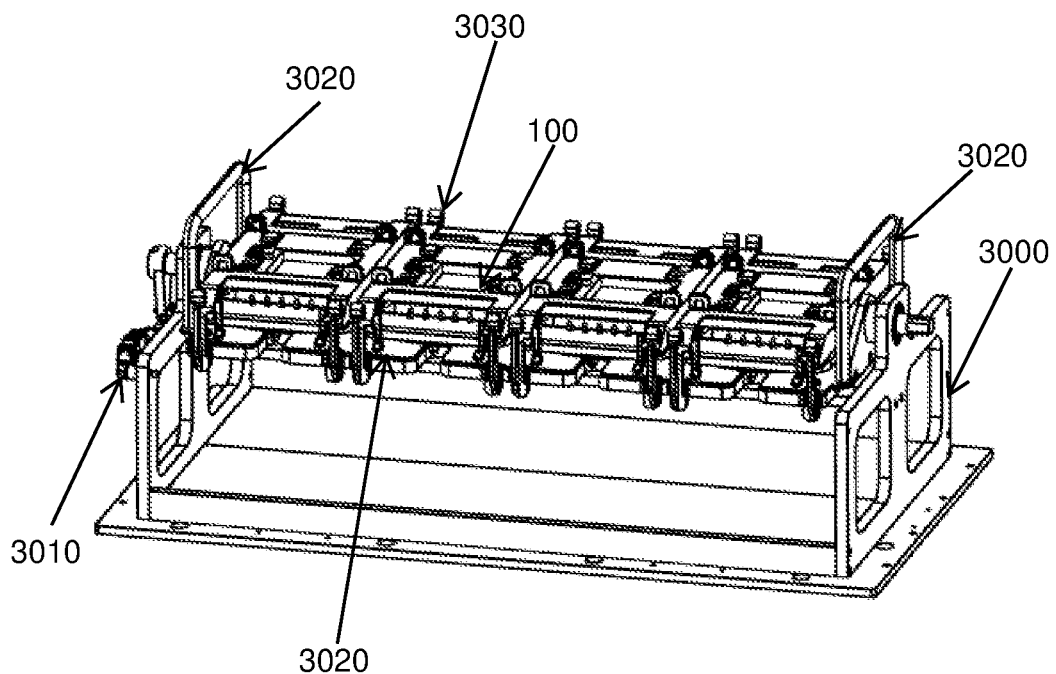
FIG. 8H is a front view of a tilt based media exchange mechanism according to an exemplary embodiment of the invention.

FIG. 8H is a front view of a tilt based media exchange mechanism 3000 according to an exemplary embodiment of the invention removed from chamber 860. For improved handling a structure 3020 including metal plate with 2 handles was designed. The metal plate is shaped to allow space for the tubing of the bioreactor. For this specific design four culture containers 100 (but could be extended to more) are assembled on the metal plate. Using frames 3030, the culture containers 100 are held in place on the structure. In some embodiments, structure 3020 is assembled with one or more containers 100 and lifted into incubation chamber 860 and placed on top of tilt table 3000.

Figure 8I:
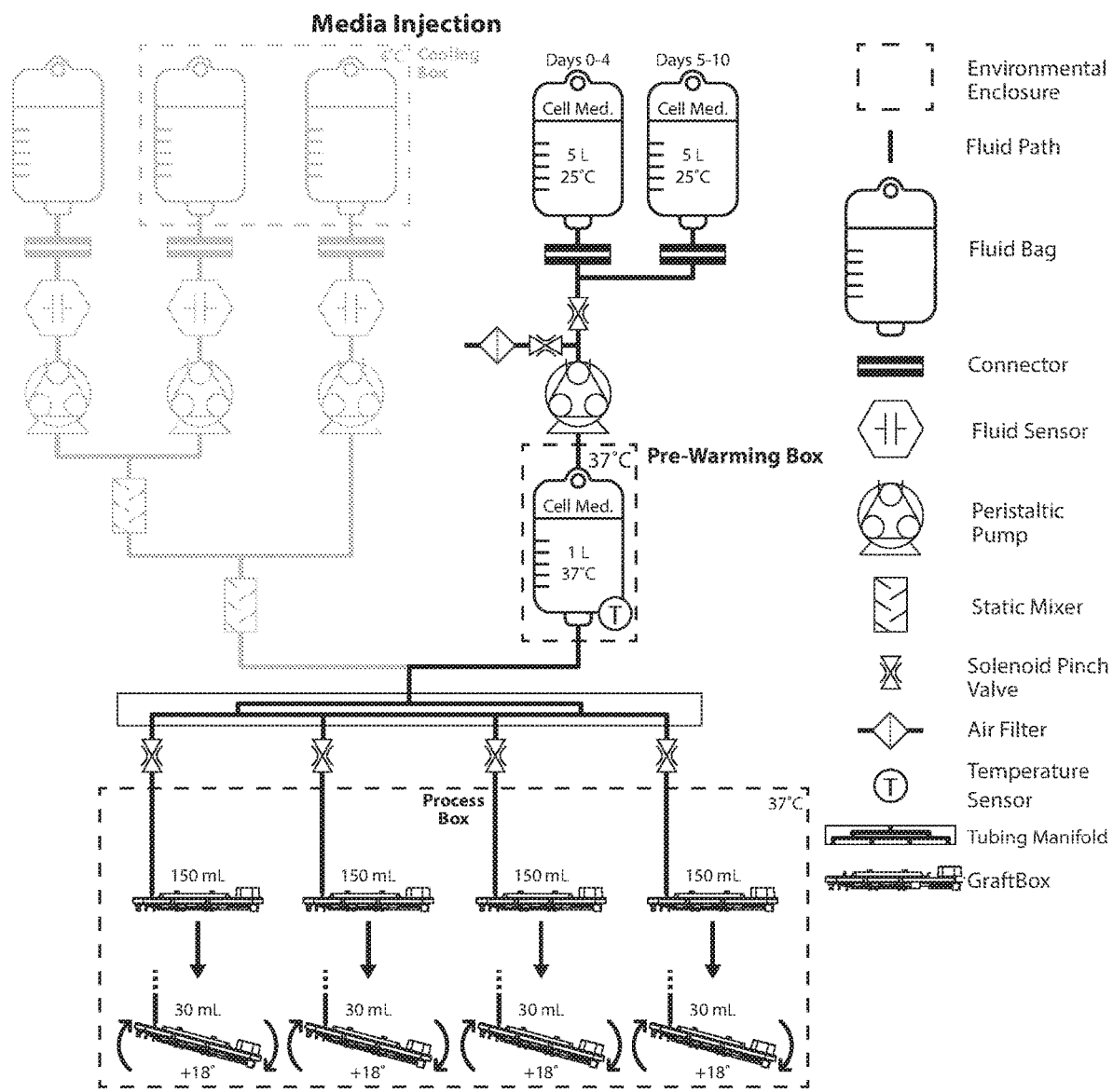
FIG. 8I is a simplified pictorial flow diagram of media injection according to an exemplary embodiment of the invention.

FIG. 8I is a simplified pictorial flow diagram of media injection according to an exemplary embodiment of the invention.

Figure 8J:
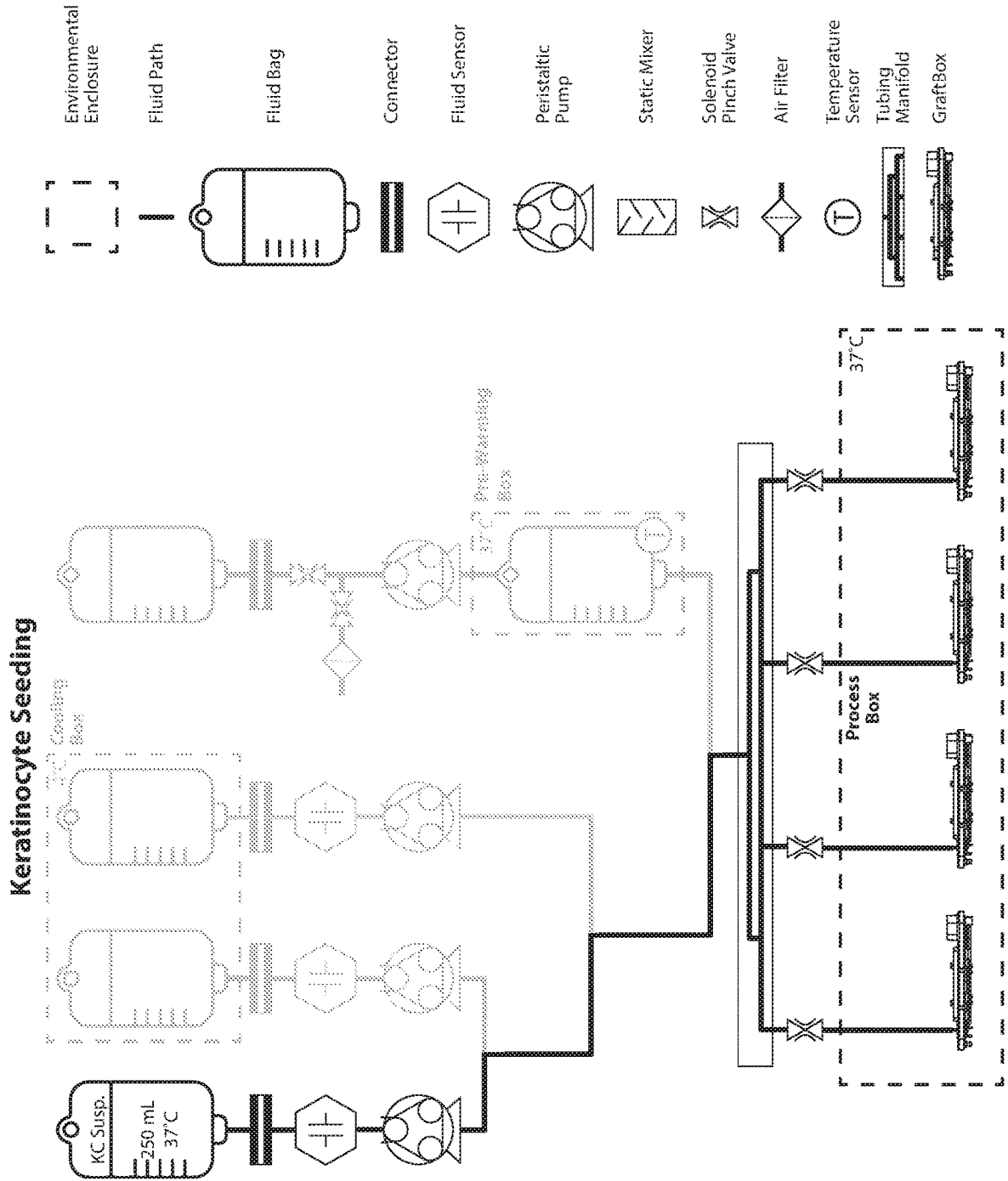
FIG. 8J is a simplified pictorial flow diagram of keratinocyte seeding according to an exemplary embodiment of the invention.
Figure 8K:
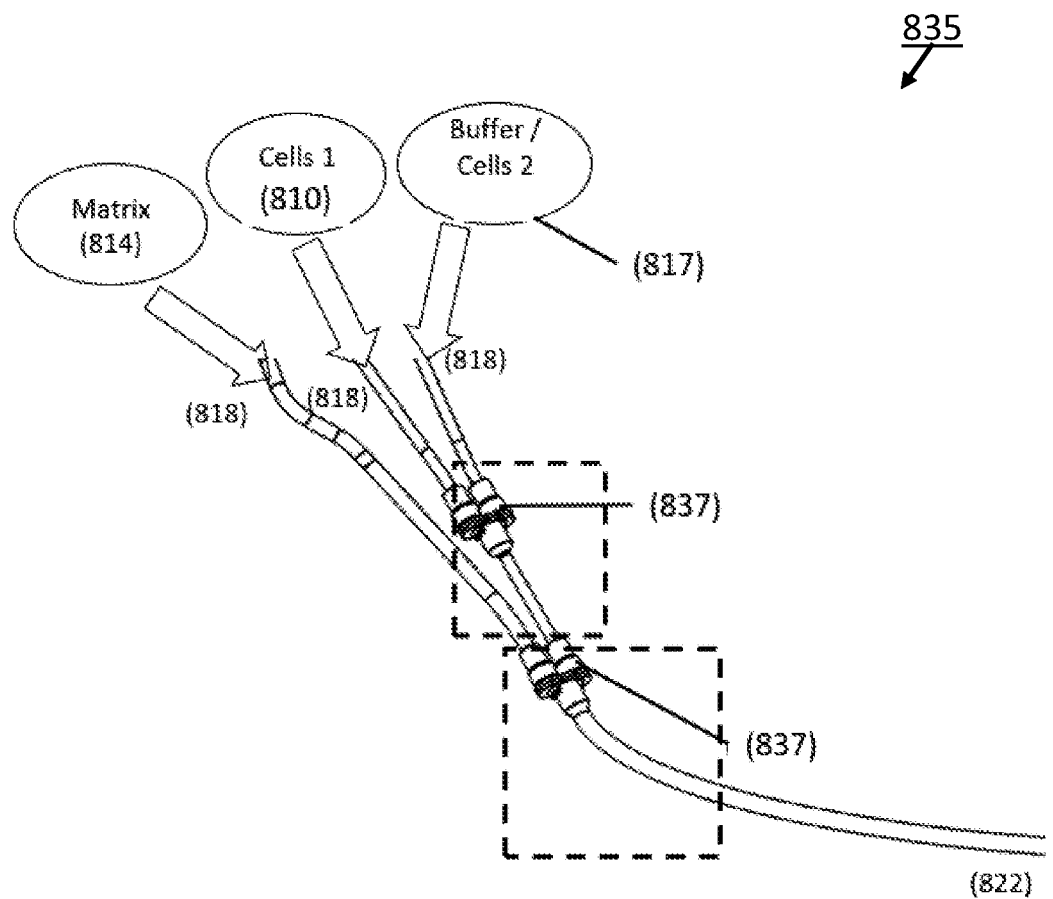
FIG. 8K is a simplified is a simplified schematic representation of a static mixer as employed in some exemplary embodiments of the invention.

FIG. 8J is a simplified pictorial flow diagram of keratinocyte seeding according to an exemplary embodiment of the invention (e.g as at 540 in FIG. 5).

FIG. 8J2 is a simplified pictorial flow diagram of hydrogel formation and Fibroblast seeding (e.g as at 510 in FIG. 5) according to an exemplary embodiment of the invention.

FIG. 8J3 is a simplified pictorial flow diagram of hydrogel incubation and compression (e.g as at 520 and 530 in FIG. 5) according to an exemplary embodiment of the invention.

Exemplary Cell Culture System

Figure 9A:
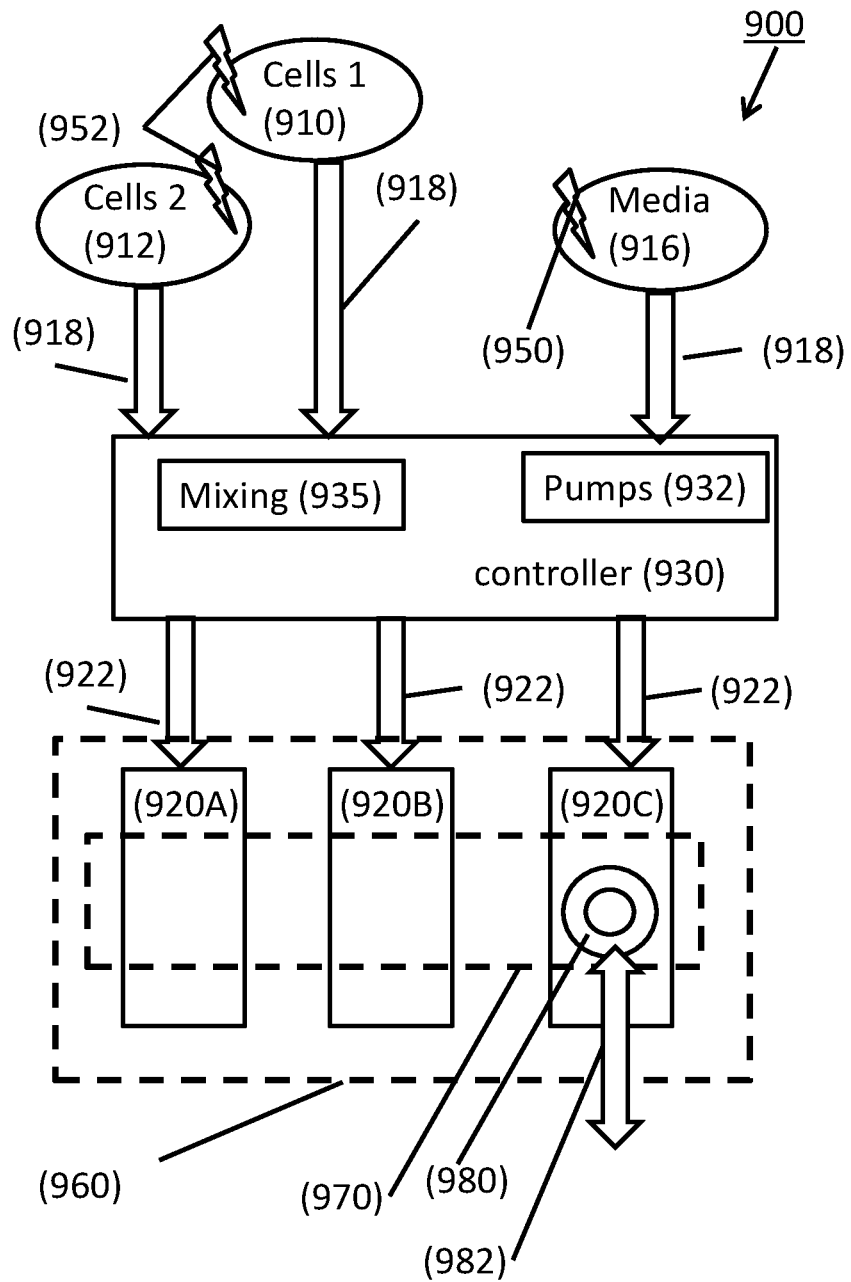
FIG. 9A is a simplified schematic representation of a cell culture system according to an exemplary embodiment of the invention.

FIG. 9A is a simplified schematic representation of a cell culture system, indicated generally as 900, according to an exemplary embodiment of the invention. Depicted exemplary system 900 includes a plurality of cell culture containers (e.g. 920A; 920B and 920C), reservoirs for cell suspension 910 and culture media 916 and; conduits (e.g. 918 and 922) connecting each of the reservoirs to each of the culture containers. In the depicted embodiment, a controller (930) is configured to deliver cell suspension 910 and culture media 916 through conduits 918 and 922 to culture containers 920A; 920B and 920C in a coordinated manner to produce cultures in the containers. For clarity, only three culture containers are depicted although a larger number would typically be present.

In some exemplary embodiments of the invention, reservoirs (910 and/or 912) for cell suspensions contain at least one cell type selected from the group consisting of fibroblasts (FB), keratinocytes (KC), adipocytes, myocytes, neuronal cells and stem cells. According to various exemplary embodiments of the invention the reservoirs for cell suspensions include at least two reservoirs for at least two different cell types selected from the group consisting of fibroblasts (FB), keratinocytes (KC), adipocytes, myocytes, neuronal cells, pericytes and stem cells. According to various exemplary embodiments of the invention the stem cells include epithelial stem cells and/or mesenchymal stem cells and/or Induced Pluripotent Cells (IPCs).

In some embodiments, reservoirs (910; 912) for cell suspensions contain a first cell type of epithelial origin and a second cell type selected from the group consisting of cells of mesenchymal cells, cells of dermal origin, adipocytes, myocytes, neuronal cells, pericytes and stem cells.

In some exemplary embodiments of the invention, use of multiple cell types contributes to an ability to generate tissue (soft and/or hard) and/or organs. Alternatively or additionally, according to various exemplary embodiments of the invention additional reservoirs are provided for media 916 and/or buffer and/or cell matrix. According to various exemplary embodiments of the invention contents of the various reservoirs are mixed (e.g. by mixers 935) in all possible combinations at controlled ratios. In some exemplary embodiments of the invention, program instructions for controller 930 control ratios and/or components of a mixture to be prepared.

In the depicted embodiment, reservoirs 910 and/or 912 for cell suspension and or reservoir 916 for culture media each include a temperature control mechanism (950 and/or 952). In some exemplary embodiments of the invention, the temperature control mechanism comprises a Peltier element which can heat and/or cool. In the depicted embodiment, controller 930 includes pumps 932 to move the cell suspension(s) and culture media through the conduits. In some exemplary embodiments of the invention, the pumps are external to the controller.

Figure 9B:
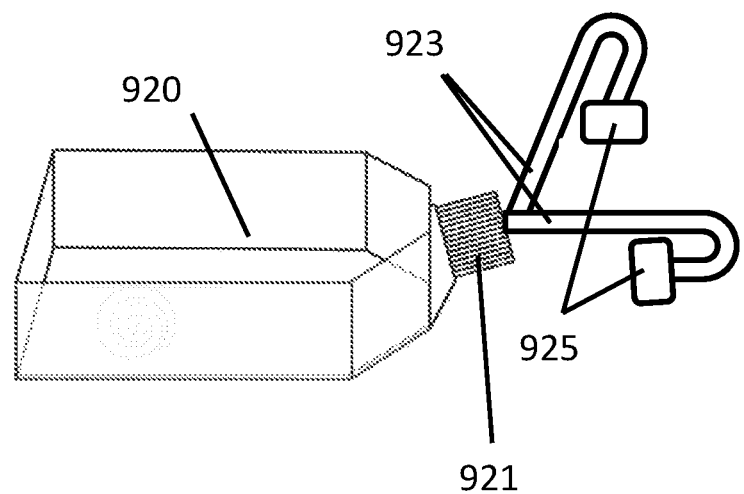
FIG. 9B is a schematic representation of adaptation of a standard tissue culture container for use in cell culture system according to an exemplary embodiment of the invention.

In some exemplary embodiments of the invention, system 900 includes connectors for attachment of conduits 922 to cell culture containers (920A; 920B and 920C) as depicted in FIG. 9B.

Depicted exemplary system 900 includes an incubation chamber 960 designed and configured to contain the plurality of tissue culture containers (920A; 920B and 920C). In some exemplary embodiments of the invention, incubation chamber 960 is equipped with control mechanisms for temperature and/or humidity and/or $CO_2$ as discussed hereinabove and hereinbelow.

In the depicted embodiment, system 900 includes a camera 980 and bidirectional data communication link 982 to an external input device. In some embodiments, the external user input device displays output pictures or videos from camera 980 and includes a user interface (e.g. a graphical user interface (GUI)) for entry of commands to controller 930.

In some exemplary embodiments of the invention, controller 930 is adapted to periodically remove media from culture containers (920A; 920B and 920C) and add new media from reservoir 916. In some exemplary embodiments of the invention, controller 930 is programed with a schedule and reverse a flow direction of pumps 932 to remove media from containers 920A; 920B and 920C via conduits 922. In some embodiments, removed media is pumped to a waste container. Although a single set of conduits 922 is depicted for simplicity, in some embodiments, separate conduits 922 are provided for waste removal and introduction of fresh media.

In the depicted embodiment, system 900 includes a compression mechanism 970 operable by controller 930 to compress a gel matrix in one or more of containers 920A; 920B and 920C.

FIG. 9B is a schematic representation of adaptation of a standard tissue culture container for use in cell culture system according to an exemplary embodiment of the invention. FIG. 9B depicts a tissue culture flask 920 fitted with a cover 921 through which tubing (conduits) 923 pass. In the depicted embodiment, distal ends of tubing 923 are fitted with aseptic connectors 925. In some embodiments, ASEPTQUICK connectors are used as 925. According to various exemplary embodiments of the invention tubing 923 is used to introduce/remove media from flask 920 and/or to introduce a humidified mixture of air and $CO_2$. Alternatively or additionally, in some embodiments, tubing 923 is connected to pumps 932 (FIG. 9A). In other exemplary embodiments of the invention, a roller bottle is used instead of flask 920.

Exemplary Pump Based Media Exchange System

Figure 10:
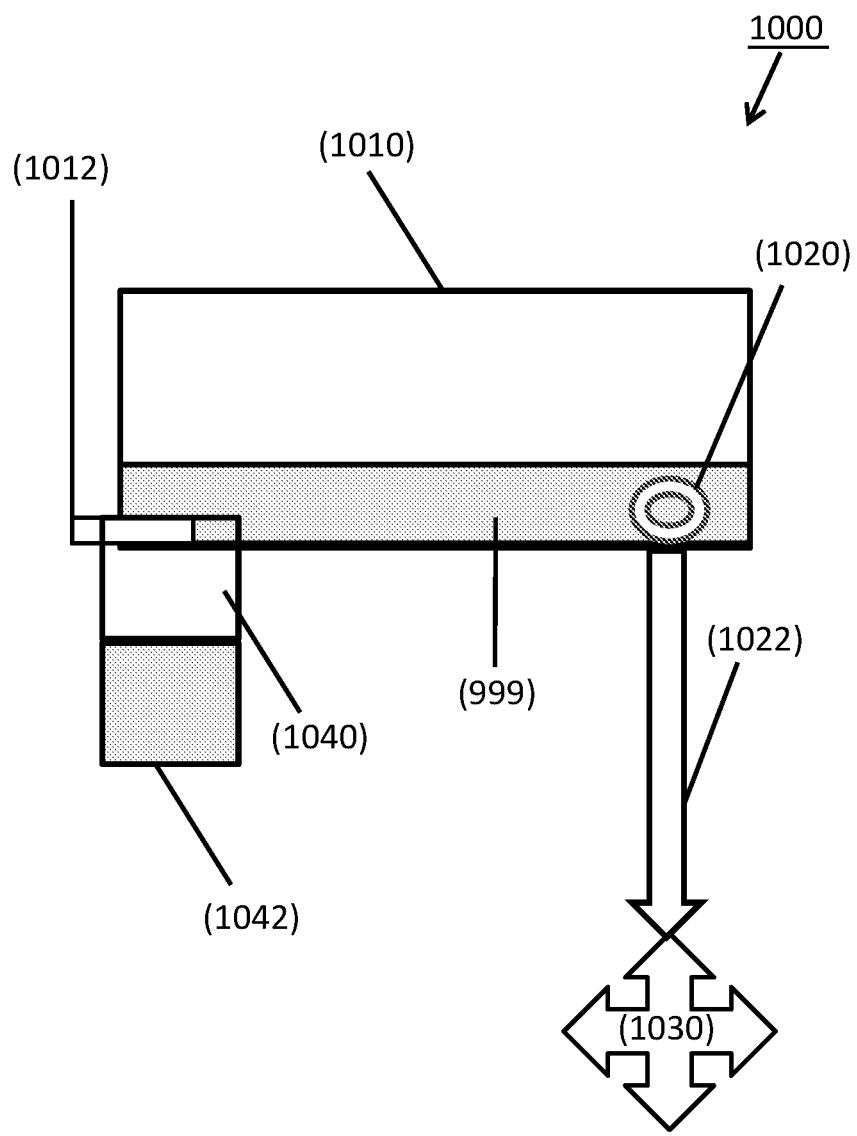
FIG. 10 is a simplified schematic representation of a media exchange system for cell culture according to an exemplary embodiment of the invention.

FIG. 10 is a simplified schematic representation of a media exchange system, indicated generally as 1000, for cell culture according to an exemplary embodiment of the invention.

Depicted exemplary system 1000 includes a cell culture container 1010 equipped with at least one port 1012, a detector 1020 measuring a parameter of media 999 in container 1010 and producing an indicator signal 1022. In the depicted embodiment, system 1000 includes a media exchange mechanism including a controller 1030 configured to respond to a threshold value of indicator signal 1022 by operating a pump 1040 that withdraws spent media via at least one port 1012 and introduces fresh media 1042 via at least one port 1012. According to various exemplary embodiments of the invention the parameter is selected from the group consisting of pH, $CO_2$ concentration, glucose concentration, lactate concentration, and non adherent cells (number and/or percentage). Alternatively or additionally, according to various exemplary embodiments of the invention Detector 1020 includes a pH electrode and/or a camera. In some exemplary embodiments of the invention, a change in pH of media 999 changes a color of a pH indicator in the media that produces a machine readable change in a digital output signal from a camera acting as detector 1020.

Alternatively or additionally, in some embodiments, detector 1020 measure solutes dissolved in the culture media (e.g. glucose and or lactate). In some embodiments, measurement of a solute dissolved in culture media is accomplished with a biosensor employing an enzyme-based amperometric measurement mechanism. In some exemplary embodiments of the invention, cell culture container 1010 is a graft culture vessel 100 as described hereinabove. In other exemplary embodiments of the invention, cell culture container 1010 is a tissue culture flask 920 (FIG. 9B) or roller bottle.

Exemplary Humidified $CO_2$ Supply System

Figure 11:
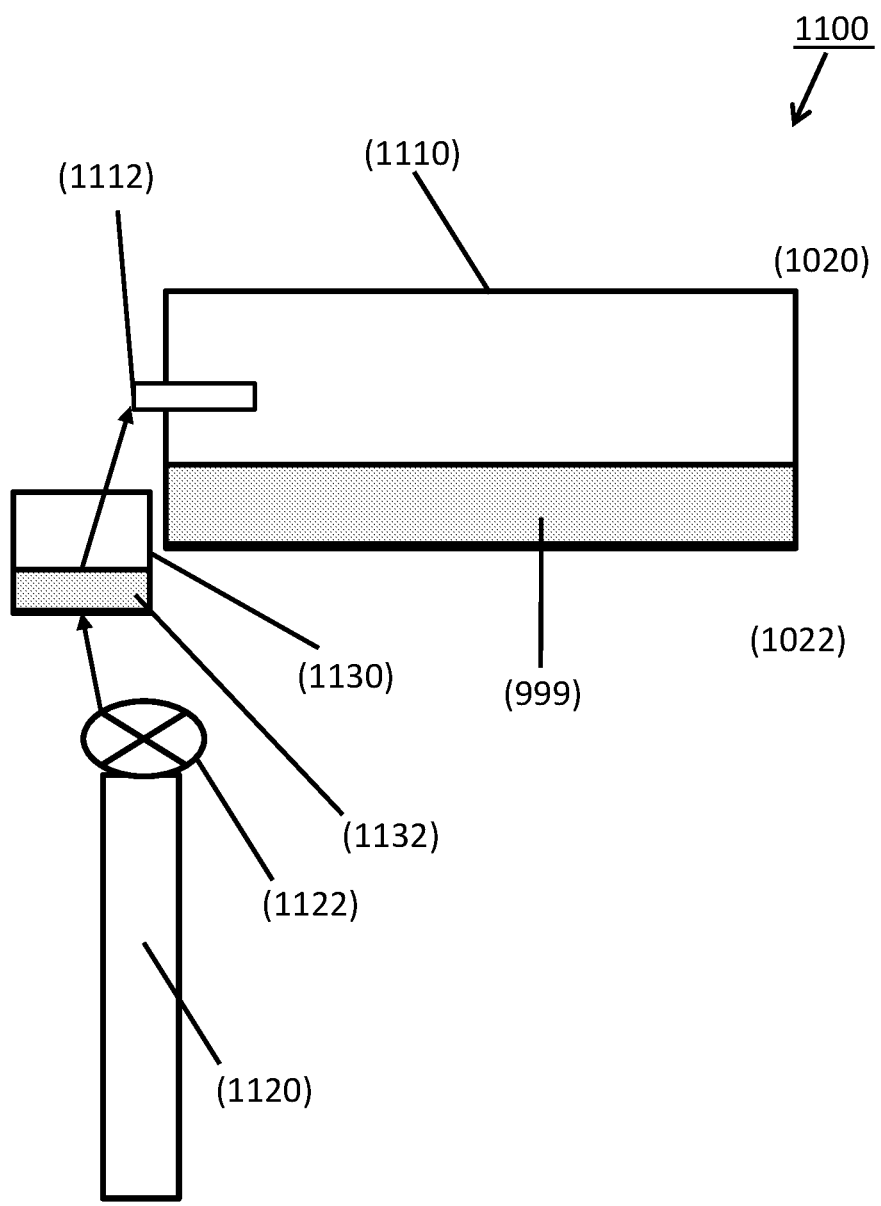
FIG. 11 is a simplified schematic representation of a humidified $CO_2$ supply system for cell culture according to an exemplary embodiment of the invention.

FIG. 11 is a simplified schematic representation of a humidified $CO_2$ supply system, indicated generally as 1100 for cell culture according to an exemplary embodiment of the invention. Depicted exemplary system 1100 includes a closed cell culture container 1110 equipped with at least one gas port 1112. In the depicted embodiment, container 1110 is partly filled with media 999. In the depicted embodiment, system 1100 includes a $CO_2$ tank 1120 connected via a regulator 1122 to the at least one gas port 1112 and a water reservoir 1130 partially filled with water 1132 though which $CO_2$ from tank 1120 passes between regulator 1122 and at least one gas port 1112. According to the depicted embodiment, as gas from regulator 1122 bubbles through water 1132 in reservoir 1130 it is humidified. In some exemplary embodiments of the invention, closed cell culture container 1110 is a graft culture vessel 100 as described hereinabove.

Exemplary Tilt Based Media Exchange System

FIG. 12A is a simplified schematic representation of tilt based media exchange system, indicated generally as 1200, for graft culture according to an exemplary embodiment of the invention.

FIG. 12B is a simplified pictorial flow diagram of a tilt based media exchange system, indicated generally as 1201, for graft culture according to an exemplary embodiment of the invention;

Depicted exemplary system 1200 includes a support surface 1210 for a plurality of tissue culture vessels 100 and a tilt mechanism 1220 controlling an angle of support surface; 1210 and a controller 1230 configured to operate mechanism 1220 to provide controlled removal of media from containers 100 through one or more ports.

In some embodiments, support surface 1210 is installed in an incubation chamber 860 as described hereinabove.

In some exemplary embodiments of the invention, controller 1230 is configured to operate tilt mechanism 1220 to +18°, and then to −30° to drain media into a waste container as depicted in FIG. 12 B. In FIG. 12B, the (+) or (−) of the angle is defined by the direction of container 100. When surge compartments 441 rise, the angle is (−). When surge compartments 441 drop, the angle is (+). Alternatively or additionally, in some embodiments controller 1230 is configured to operate tilt mechanism 1220 to −5° to facilitate sampling as depicted in FIG. 12B.

Alternatively or additionally, in some embodiments controller 1230 is configured to operate tilt mechanism 1220 to tilt to +18° to remove medium from the top compartment of container 100 to surge compartment 441. The tilt mechanism then returns via its default position 0° to −30° angle. Given the design of container 100, media above the standard media level at 0° automatically flows into the waste bag. Therefore, media does not re-enter the top compartment. At 30° tilt angle all media will exit container 100. In the specific configuration of container 100, media from the top compartment is always removed via the bottom compartment.

Figure 12C:
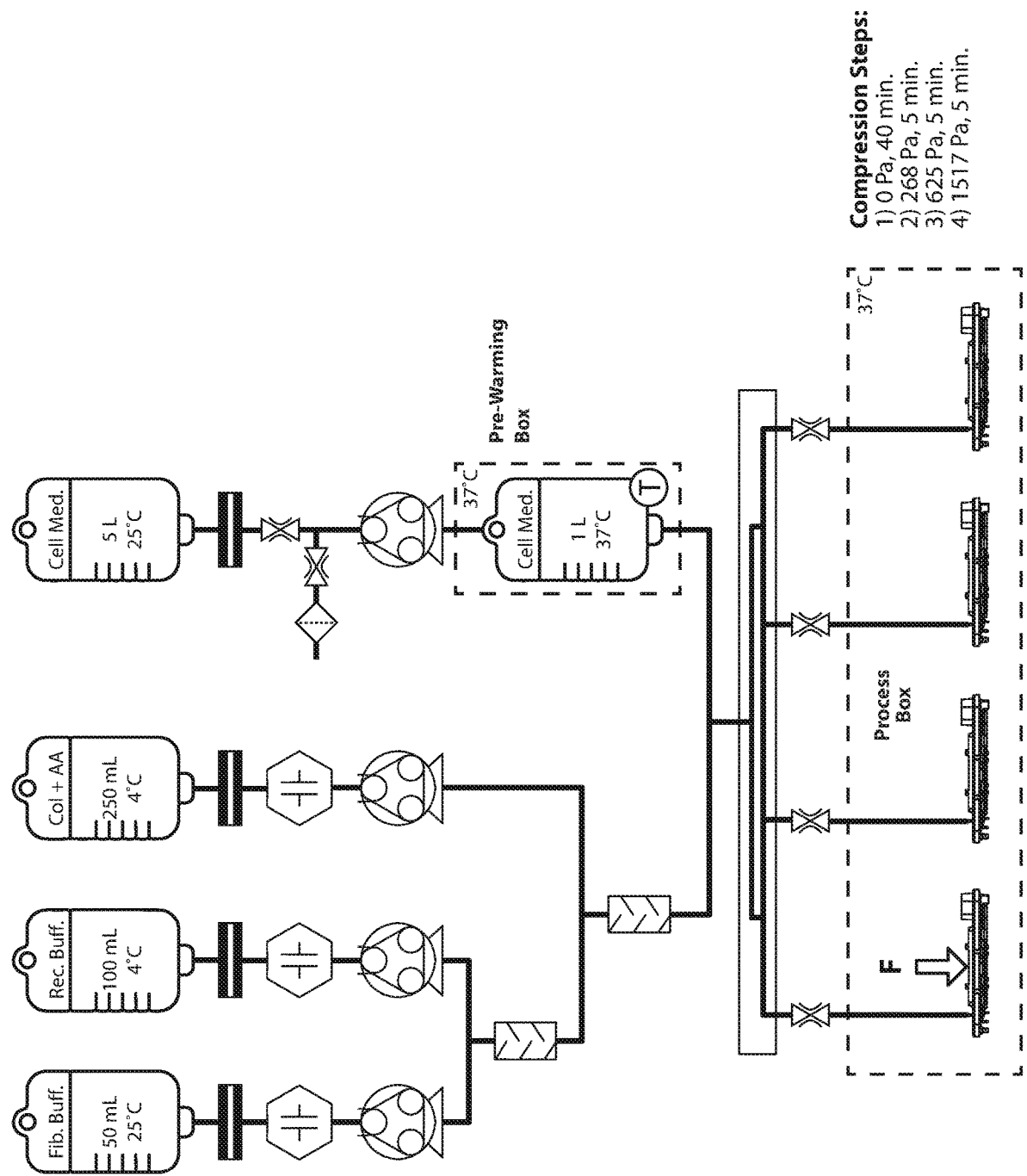
FIG. 12C is a simplified pictorial flow diagram of system for cell culture according to an exemplary embodiment of the invention (Icons are as in FIGS. 8J. 8J2 and 8J3)

FIG. 12C is a simplified pictorial flow diagram of system for cell culture according to an exemplary embodiment of the invention (Icons are as in FIGS. 8J. 8J2 and 8J3). The processes depicted in FIG. 12C are similar to those described in the context of FIG. 8J3.

Exemplary Compression Module

FIG. 13A is a simplified schematic representation of a compression module, indicated generally as 1300, for a graft culture system according to an exemplary embodiment of the invention.

FIG. 13B is a front view of a compression module, indicated generally as 1301, for a graft culture system according to an exemplary embodiment of the invention with an inset showing a piston assembly, indicated generally as 1311, in isolation.

Depicted exemplary system 1300 includes a plurality of graft culture containers 100, each container having a movable plunger 431 in a lid 400 thereof. (See FIG. 4A and FIG. 4B and accompanying description hereinabove). In the depicted embodiment, system 1300 includes at least one piston 1310 and a controller 1320 configured to operate a vertical displacement mechanism 1330 to lower and raise piston 1310 to depress and release each of plungers 431 in lids 400 of containers 100.

In some embodiments, system 1300 includes a horizontal displacement mechanism (1332). According to these embodiments controller 1320 aligns the at least one piston 1310 with at least one plunger 431.

In some exemplary embodiments of the invention, all of containers 100 are in a single line and a corresponding number of pistons 1310 is provided in a matching line. In this configuration, either no horizontal displacement is required, or a single horizontal displacement brings the line of pistons 1310 into alignment with the line of containers 100. In either case, when vertical displacement mechanism 1330 lowers pistons 1310, all of plungers 431 are depressed concurrently. When vertical displacement mechanism 1330 raises pistons 1310, all of plungers 431 are released concurrently. This is single cycle parallel operation.

In some exemplary embodiments of the invention, all of containers 100 are in a single line or in parallel lines and a smaller number of pistons 1310 is provided. In the simplest case, a single piston 1310 is provided. In this configuration, horizontal displacement is required to sequentially bring piston(s) 1310 into alignment with plunger(s) of container(s) 100. Each time vertical displacement mechanism 1330 lowers piston(s) 1310, additional plunger(s) 431 are depressed. When vertical displacement mechanism 1330 raises piston (s) 1310, all of the depressed plunger(s) 431 are released concurrently. This is sequential operation.

In some exemplary embodiments of the invention, containers 100 are in parallel rows and a number of pistons 1310 corresponding to the number of containers in a row is provided. In this configuration, horizontal displacement is required to sequentially bring piston(s) 1310 into alignment a next row after each round of operation. Each time vertical displacement mechanism 1330 lowers piston(s) 1310, plungers 431 in one row are depressed. When vertical displacement mechanism 1330 raises pistons 1310, all of the depressed plungers 431 in that row are released concurrently. This is multi-cycle parallel operation.

Regardless of the mode of operation, depression of a plunger 431 by a piston 1310 compresses the hydrogel matrix in container 100. In some exemplary embodiments of the invention, vertical displacement mechanism 1330 is adjustable for different forces and compression patterns (e.g. linear, stepwise).

For example, in some embodiments, force is initially increased to a $1^{st}$ stop, held for some time, then increased to a second stop. For example, Stop 1: 268 Pa, hold 5 minutes; increase to Stop 2: 625 Pa, hold 5 minutes; increase to Stop 3: 1517 Pa and hold 5 minutes.

In other exemplary embodiments of the invention, piston 1310 continuously increases the force until the final force is reached and held. For example, in some embodiments, piston 1310 applies a continuously increasing pressure at a rate of 4 Pa per second until after 15 minutes 1517 Pa are reached and a final hold at 1517 Pa for 5 minutes.

Alternatively or additionally, in some embodiments controller 1320 is programmable (e.g. for horizontal displacement patters). Alternatively or additionally, in some embodiments system 1300 includes a pressure sensor 1340. Alternatively or additionally, in some embodiments system 1300 includes a camera 1340 on piston 1310. In some embodiments, compression causes the movement of 200 (See FIG. 1A; 2A; 2B and corresponding text) in container 100. When the desired stage of compression is reached 230 and 232 are in a position that is visually marked within container 100. This position is detected by a camera (e.g. 1340 and/or 880 in FIG. 8A and/or 980 in FIG. 9) which provides out put to controller 1320. Controller 1320 translates the camera output into a stop signal. In the current embodiment the camera is located on the compression system to align with container 100 and to be used for visual checks and is not involved in compression per se.

FIG. 13B depicts an exemplary compression module 1301 which is inserted from the top into an environmental chamber (e.g. 860 in FIG. 8B) in some embodiments of the invention it is fixed there as part of the device. In the depicted design four pistons 1311 are set up in a line under control of four controllers 1321 equipped with vertical displacement mechanisms 1331, to compress four hydrogels. Controllers 1321 generate a specified force by lowering pistons 1311 using vertical displacement mechanisms 1331. Pressure sensors 1341 monitor the pressure build up. This pressure is transferred via springs 1350 onto the pressure plate 1352 of piston heads 1354. In some embodiments, piston heads 1354 are attached first to graft culture containers 100, then to pistons 1311. In some exemplary embodiments of the invention, springs 1350 are removable part and not fixed to piston 1311 or container 100.

In some embodiments, once graft culture containers 100 are filled with hydrogel and are placed in the incubation chamber, piston heads 1354 are placed onto containers 100. Pins 1360 fit into matching connection points in containers 100. In the depicted embodiment, pressure generated by 1321/1331 is transferred through springs 1350 to pressure plate 1352. and from there via four pins 1360 evenly onto plungers 431 in covers 430 of containers 100 (see FIG. 13A).

In the depicted embodiment, a camera 1343 is secured in place by a Camera holder 1344. The camera allows capture of photographs of the 3D tissue culture (not microscopic pictures).

Exemplary Remote Control System

Figure 14:
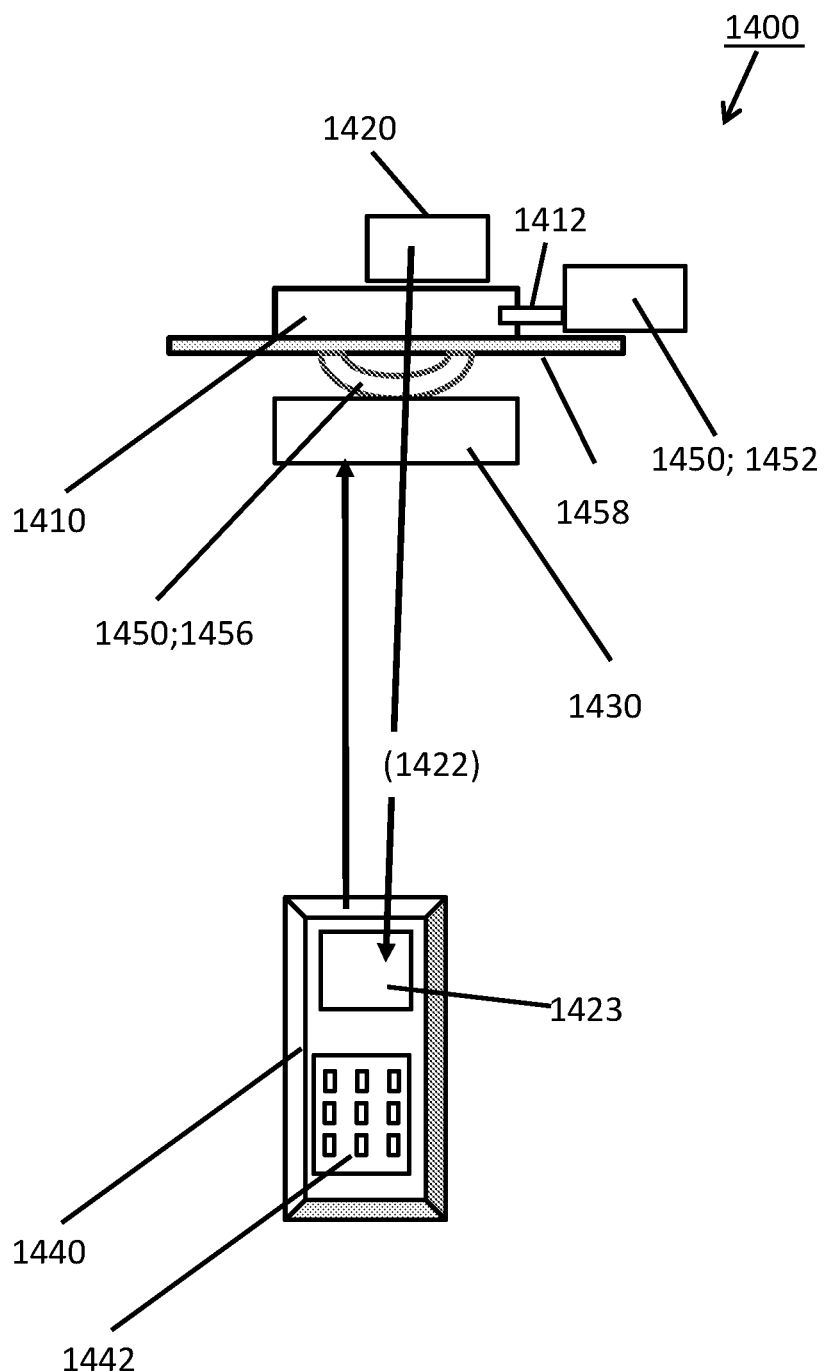
FIG. 14 is schematic representation of a graft culture system adapted for remote operation according to an exemplary embodiment of the invention.

FIG. 14 is schematic representation of a graft culture system, indicated generally as 1400, adapted for remote operation according to an exemplary embodiment of the invention. Depicted exemplary system 1400 includes a tissue culture container 1410 with at least one port 1412 and a camera 1420 providing image output 1422 of a culture in container 1410 and a controller 1430 exercising control over a media exchange mechanism 1450.

In some exemplary embodiments of the invention, image output 1422 is received by a remote device 1440 and displayed to a user of device 1440 on display 1423. The user then employs user interface 1442 for operation of controller 1430.

In the depicted embodiment, the media exchange mechanism 1450 includes at least one pump 1452 that withdraws spent media via the at least one port 1412 and introduces fresh media via the at least one port.

Alternatively or additionally, in some embodiments media exchange mechanism 1450 includes a tilt mechanism 1456 controlling an angle of a support surface 1458 holding tissue culture container 1410. Use of tilt mechanisms such as 1450 is described hereinabove in the context of FIG. 12A and FIG. 12B.

In some exemplary embodiments of the invention, exchange mechanism 1450 is used to remove a sample of media for analysis as depicted in FIG. 12B. According to various exemplary embodiments of the invention metabolic indicators such as glucose and/or lactate are analyzed. In some exemplary embodiments of the invention, pump 1452 pumps the sample to an analytic device (not depicted). In other exemplary embodiments of the invention, a biosensor (not depicted) is deployed in container 1410 and provides an output signal to remote device 1440.

Exemplary Environmental Control System

Figure 15:
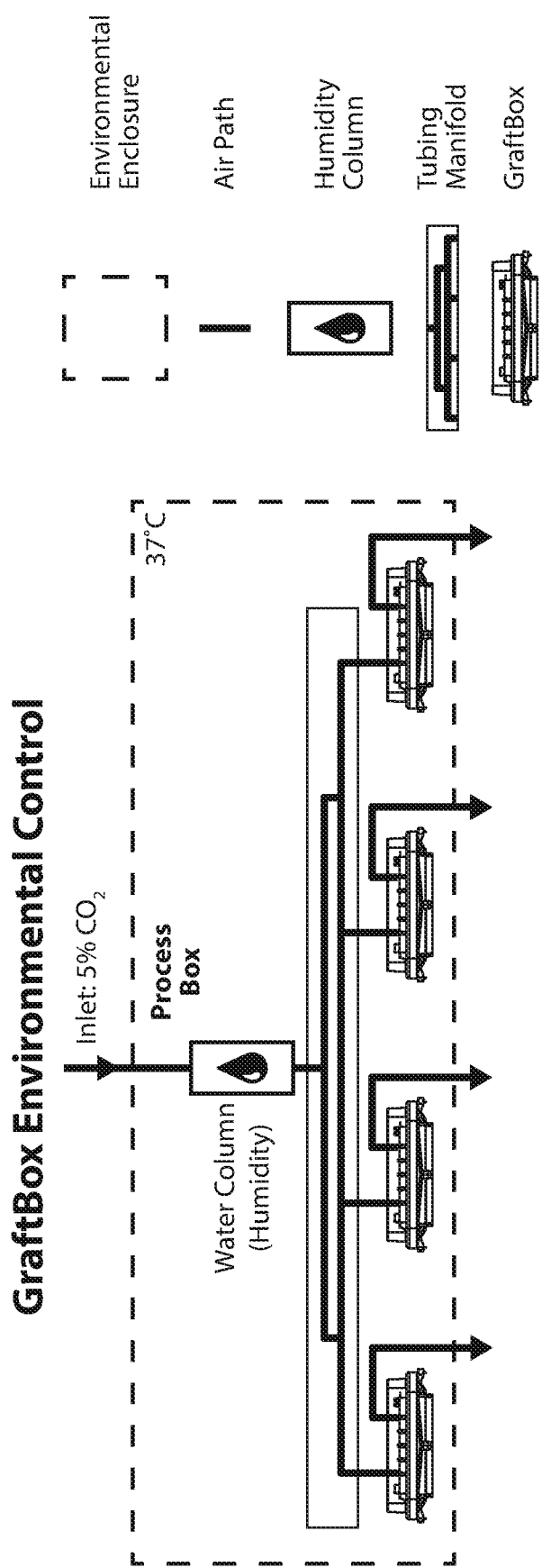
FIG. 15 is a simplified pictorial flow diagram of an environmental control system for cell culture according to an exemplary embodiment of the invention.

FIG. 15 is a simplified pictorial flow diagram of an environmental control system for cell culture according to an exemplary embodiment of the invention. FIG. 15 demonstrates how a tubing manifold is employed to delver air of a desired temperature/CO2 content and humidity to a plurality of graftboxes (tissue culture vessels 100 in other drawings).

Exemplary Use Scenarios

While much of the above description relates to dermal fibroblasts and epidermal keratinocytes, other cells types isolated from Human or animal tissues from different origin are employed in additional embodiments of the invention. Fibroblast cell strains (Human or animal) are routinely derived from sources, including, but not limited to dermis, tendon, lung, umbilical cords, cartilage, urethra, corneal stroma, oral mucosa, and intestine. The human/animal include but are not limited to fibroblasts, smooth muscle cells, chondrocytes and other connective tissue cells of mesenchymal origin. In some exemplary embodiments of the invention, fibroblasts are isolated by microdissection from the dermal papilla of hair follicles. In some exemplary embodiments of the invention, a corneal-construct is produced using the matrix-producing cells derived from corneal stroma. In some exemplary embodiments of the invention, cell donors vary in development and age. Alternatively or additionally, in some embodiments cells are derived from donor tissues of embryos, neonates, or older individuals including adults. In some exemplary embodiments of the invention, embryonic progenitor cells such as mesenchymal stem cells are used in embodiments of the invention and induced to differentiate to develop into a desired tissue using known differentiation factors and/or differentiation conditions.

Alternatively or additionally, Human or animal epithelial cells are sources included but not limited to Human or animal epidermis, skin, lung, umbilical cords, urethra, corneal stroma, oral mucosa, intestine, bladder, esophagus and cornea.

Although human cells are used in many embodiments of the invention, animal cells are also used in many embodiments. Cells from other mammalian species including, but not limited to, equine, canine, porcine, bovine, ovine sources and rodent species (e.g. mouse and/or rat and/or rabbit) are also used. In addition, cells that are spontaneously, chemically or virally transfected or recombinant cells or genetically engineered cells are used in some embodiments of the invention. For those embodiments that incorporate more than one cell type, chimeric mixtures of normal cells from two or more sources; mixtures of normal and genetically modified or transfected cells; or mixtures of cells of two or more species or tissue sources are used in different embodiments of the invention.

It is expected that during the life of this patent many cell culture media, membrane types and polymers will be developed and the scope of the invention includes all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, module, process or element which is not specifically disclosed herein.

Specifically, the invention has been described in the context of ex-vivo production of skin grafts but might also be used to produce implants of other tissue types amenable to production in a compressed hydrogel and/or for tissue production for applications other than transplantation.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

The invention claimed is:

1. A tissue culture vessel (100) comprising:
   (a) a graft support tray (200);
   (b) a box having a lid (400) and a base (300), said box engaging and retaining said tray;
   wherein said tray has two operational states:
   a first operational state in which a floor of said tray is slightly raised with respect to a floor of said base; and
   a second operational state in which said floor of said tray descends to contact the floor of said base;

wherein said graft support tray (200; 201) comprises:
(a) a rigid frame (210);
(b) a liquid permeable membrane floor (220) attached to a lower edge (212) of said frame; and
(c) a first set of normally extended springs (230) attached externally to two opposite sides of said frame.

2. A tissue culture vessel according to claim 1, comprising:
a moveable plunger attached to said lid.

3. A tissue culture vessel according to claim 1, comprising:
one or more surge compartments.

4. A tissue culture vessel according to claim 1, wherein said graft support tray comprises:
a second set of normally extended springs (232) in an opposite orientation attached to the first springs.

5. A tissue culture vessel according to claim 1, wherein said base (300; 301) comprises:
a compression structure (310) designed and configured to support a membrane floor of a graft support frame fully descended in the base; said compression structure comprising a pattern molded into the base to permit flow of media outwards as said frame descends.

6. A tissue culture vessel according to claim 1, wherein said base comprises:
indentations (320) sized and positioned to accommodate one set of springs of a graft support tray seated in the base.

7. A tissue culture vessel according to claim 1, wherein said base comprises:
indentations (320) sized and positioned to accommodate two set of springs of a graft support tray seated in the base.

8. A tissue culture vessel according to claim 1, wherein said base comprises pins (330) or holes sized and positioned to engage corresponding holes or pins provided on a graft support tray positioned in said base.

9. A tissue culture vessel according to claim 1, wherein said base comprises: an O-ring (340) or other gasket or an overmolded elastomer.

10. A tissue culture vessel according to claim 1, wherein said base comprises: at least one liquid removal port (344; 346).

11. A tissue culture vessel according to claim 1, wherein said base comprises:
snap to fit connectors (350) for attachment to a lid.

12. A tissue culture vessel (100) comprising:
(a) a graft support tray (200);
(b) a box having a lid (400) and a base (300), said box engaging and retaining said tray;
wherein said tray has two operational states:
a first operational state in which a floor of said tray is slightly raised with respect to a floor of said base; and
a second operational state in which said floor of said tray descends to contact the floor of said base; wherein said lid comprises:
(a) a rigid frame (410); and
(b) a flexible bellows (420) deployed within said frame, said bellows holding a plunger (431) in a fixed orientation with respect to said frame; and
wherein said lid comprises one or more surge compartments (440) extending above a plane of an upper edge of said frame.

13. A tissue culture vessel (100) comprising
(a) a graft support tray (200);
(b) a box having a lid (400) and a base (300), said box engaging and retaining said tray;
wherein said tray has two operational states:
a first operational state in which a floor of said tray is slightly raised with respect to a floor of said base; and
a second operational state in which said floor of said tray descends to contact the floor of said base
wherein said lid comprises:
(a) a rigid frame (410); and
(b) a flexible bellows (420) deployed within said frame, said bellows holding a plunger (431) in a fixed orientation with respect to said frame, wherein said lid comprises:
snap hooks (450) on said rigid frame sized and positioned to engage a base covered by said lid; and
wherein said lid comprises: one or more external barbed connectors (460) in fluid communication with internal outlet ports (462).

* * * * *